(12) United States Patent
Ohsedo

(10) Patent No.: US 9,744,512 B2
(45) Date of Patent: Aug. 29, 2017

(54) GELATOR AND ORGANOGEL

(71) Applicants: KYUSHU UNIVERSITY, Fukuoka-shi, Fukuoka (JP); NISSAN CHEMICAL INDUSTRIES, LTD., Tokyo (JP)

(72) Inventor: Yutaka Ohsedo, Fukuoka (JP)

(73) Assignees: KYUSHU UNIVERSITY, Fukuoka-Shi, Fukuoka (JP); NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 14/767,496

(22) PCT Filed: Feb. 13, 2014

(86) PCT No.: PCT/JP2014/053375
§ 371 (c)(1),
(2) Date: Aug. 12, 2015

(87) PCT Pub. No.: WO2014/126173
PCT Pub. Date: Aug. 21, 2014

(65) Prior Publication Data
US 2015/0375189 A1 Dec. 31, 2015

(30) Foreign Application Priority Data
Feb. 13, 2013 (JP) ................. 2013-025539

(51) Int. Cl.
*C09K 3/00* (2006.01)
*B01J 13/00* (2006.01)
(Continued)

(52) U.S. Cl.
CPC .......... *B01J 13/0065* (2013.01); *A61K 8/042* (2013.01); *B01J 31/0249* (2013.01); *C09K 3/00* (2013.01)

(58) Field of Classification Search
CPC ..... B01J 13/0065; B01J 31/0249; C09K 3/00; A61K 8/042
See application file for complete search history.

(56) References Cited

U.S. PATENT DOCUMENTS

| | | | |
|---|---|---|---|
| 4,039,360 A | 8/1977 | Allan | |
| 5,411,798 A * | 5/1995 | Funae | G11B 5/7021 347/105 |

(Continued)

FOREIGN PATENT DOCUMENTS

| | | |
|---|---|---|
| JP | 2000256303 A | 9/2000 |
| JP | 2004025305 A | 1/2004 |

(Continued)

OTHER PUBLICATIONS

May 20, 2014 International Search Report issued in International Patent Application No. PCT/JP2014/053375.
(Continued)

*Primary Examiner* — Michael A Salvitti
(74) *Attorney, Agent, or Firm* — Oliff PLC

(57) ABSTRACT

There is provided a novel gelator which enables formation of gel by a simpler technique. A gelator including two or more alkylamide compounds of General Formula [I]:

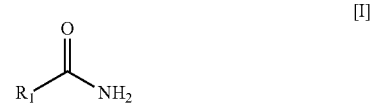

(where $R_1$ is a $C_{1-30}$ aliphatic group optionally having a substituent) or two or more alkylurea compounds of General Formula [II]:

(Continued)

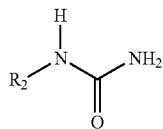

(where $R_2$ is a $C_{1-30}$ aliphatic group optionally having a substituent), wherein the gelator forms a gel exhibiting thixotropic properties.

10 Claims, 16 Drawing Sheets

(51) Int. Cl.
  *A61K 8/04* (2006.01)
  *B01J 31/02* (2006.01)

(56) References Cited

U.S. PATENT DOCUMENTS

| | | | | |
|---|---|---|---|---|
| 5,880,076 | A * | 3/1999 | Vermeer | A61K 8/42 510/119 |
| 2006/0264338 | A1* | 11/2006 | Kawamura | C10M 123/04 508/168 |
| 2007/0119340 | A1* | 5/2007 | P. Breton | C09D 11/34 106/31.43 |
| 2009/0233825 | A1* | 9/2009 | Giles | A61K 8/0295 510/123 |
| 2010/0029528 | A1* | 2/2010 | Giles | A61K 8/0295 510/123 |
| 2015/0352509 | A1* | 12/2015 | Churchfield | B01F 17/0092 516/77 |
| 2015/0375189 | A1* | 12/2015 | Ohsedo | C09K 3/00 516/102 |

FOREIGN PATENT DOCUMENTS

| | | |
|---|---|---|
| JP | 2004359643 A | 12/2004 |
| JP | 3690052 B2 | 8/2005 |
| JP | 2006307023 A | 11/2006 |
| JP | 2008515911 A | 5/2008 |
| JP | 2010077037 A | 4/2010 |
| JP | 2010111821 A | 5/2010 |
| JP | 2010272524 A | 12/2010 |
| WO | 2006042059 A1 | 4/2006 |

OTHER PUBLICATIONS

May 20, 2014 Written Opinion issued in International Patent Application No. PCT/JP2014/053375.
Mallia et al., "Robust Organogels from Nitrogen-Containing Derivatives of (R)-12-Hydroxystearic Acid as Gelators: Comparisons with Gels from Stearic Acid Derivatives," Langmuir, 2009, vol. 25, No. 15, pp. 8615-8625.
Ohsedo et al., "Mixing induced thixotropy of a two-component system of alkylurea organogelators having different alkyl chains," New Journal of Chemistry, 2013, vol. 37, No. 8, pp. 2250-2253.
Bondi, "van der Waals Volumes and Radii," The Journal of Physical Chemistry, vol. 68, No. 3, Mar. 16, 1964, pp. 441-451.
Rowland et al., "Intermolecular Nonbonded Contact Distances in Organic Crystal Structures: Comparison with Distances Expected from van der Waals Radii," J. Phys. Chem, 1996, vol. 100, No. 18, pp. 7384-7391.
Hanabusa et al., "Two-component, Small Molecule Gelling Agents," J. Chem. Soc., Chem, Commun., 1993, pp. 1382-1384.
Hirst et al., "Two-Component Gel-Phase Materials—Highly Tunable Self-Assembling Systems," Chemistry A European Journal, vol. 11, No. 19, Sep. 19, 2005, 5496-5508.
Dreiss, "Wormlike micelles: where do we stand? Recent developments, linear rheology and scattering techniques," Soft Matter, vol. 3, No. 8, 2007, pp. 956-970.
Buerkle et al., "Supramolecular gels formed from multi-component low molecular weight species," Chem. Soc. Rev., 2012, vol. 41, No. 18, pp. 6089-6102.
"Gel control-gel preparation and control of gelation-," Johokiko Co., Ltd., 2009, pp. 15-17.
Stenius et al., "Aggregation in concentrated kaolin suspensions stabilized by polyacrylate," Colloids and Surfaces, vol. 51, 1990, pp. 219-238.
Turner et al., "The Crystal Structure of Tetradecanamide," "Acta Crystallographica," vol. 8, Pt. 9, Sep. 10, 1955, pp. 551-557.
George et al., "Urea and Thiourea Derivatives as Low Molecular-Mass Organogelators," Chemistry A European Journal, 2005, vol. 11, No. 11, pp. 3243-3254.

* cited by examiner

FIG. 8

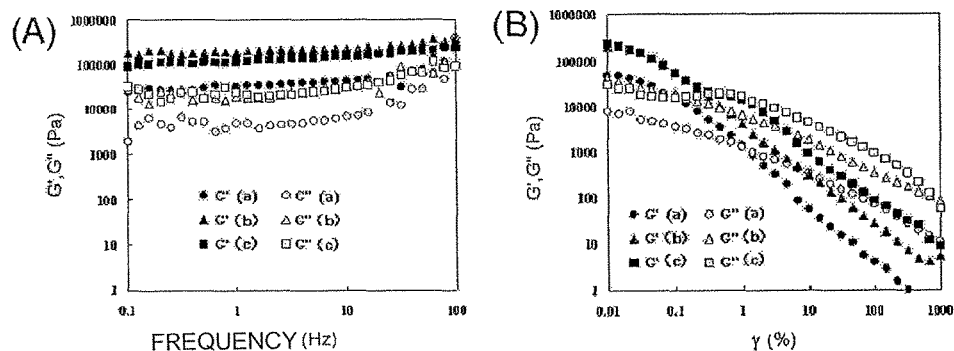

FIG. 9

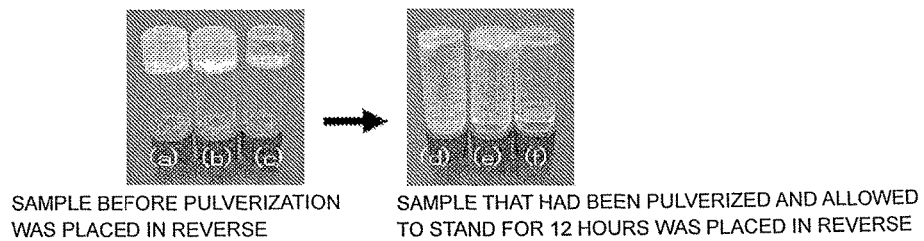

SAMPLE BEFORE PULVERIZATION WAS PLACED IN REVERSE → SAMPLE THAT HAD BEEN PULVERIZED AND ALLOWED TO STAND FOR 12 HOURS WAS PLACED IN REVERSE

FIG. 10

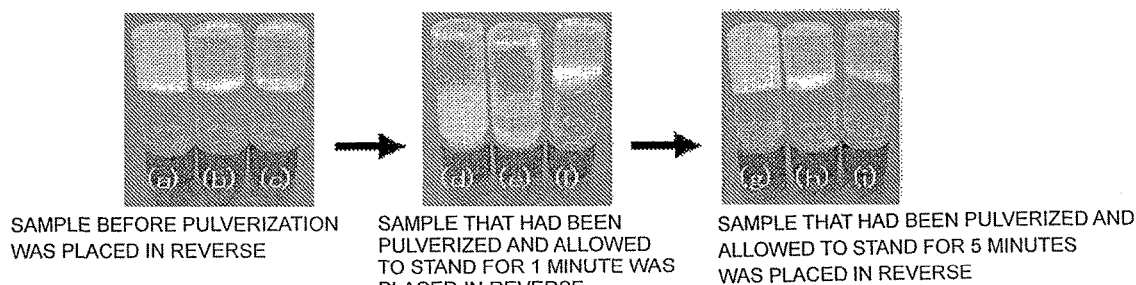

SAMPLE BEFORE PULVERIZATION WAS PLACED IN REVERSE → SAMPLE THAT HAD BEEN PULVERIZED AND ALLOWED TO STAND FOR 1 MINUTE WAS PLACED IN REVERSE → SAMPLE THAT HAD BEEN PULVERIZED AND ALLOWED TO STAND FOR 5 MINUTES WAS PLACED IN REVERSE

FIG. 11

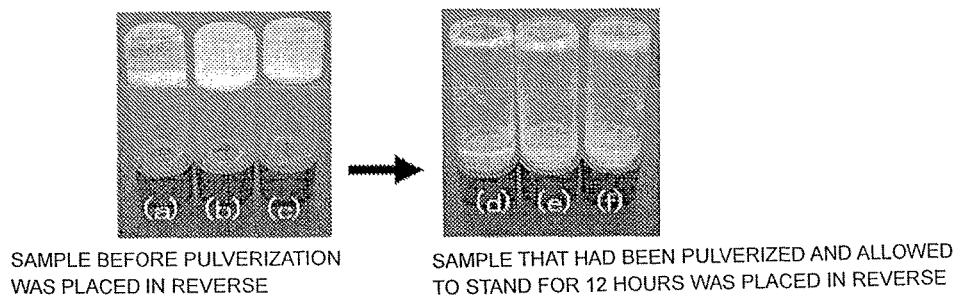

SAMPLE BEFORE PULVERIZATION WAS PLACED IN REVERSE → SAMPLE THAT HAD BEEN PULVERIZED AND ALLOWED TO STAND FOR 12 HOURS WAS PLACED IN REVERSE

FIG. 12

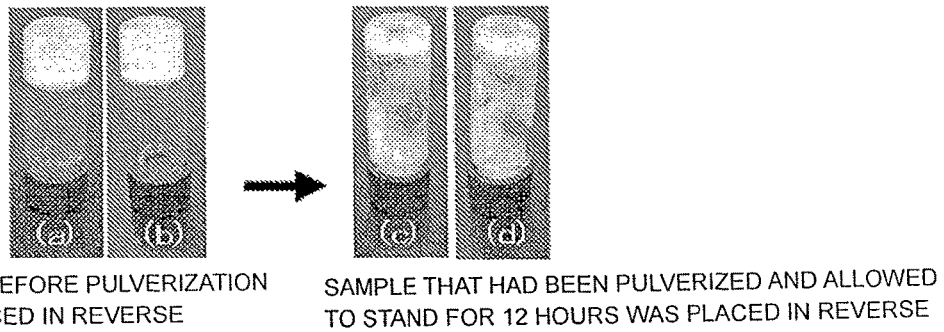

SAMPLE BEFORE PULVERIZATION
WAS PLACED IN REVERSE

SAMPLE THAT HAD BEEN PULVERIZED AND ALLOWED
TO STAND FOR 12 HOURS WAS PLACED IN REVERSE

FIG. 13

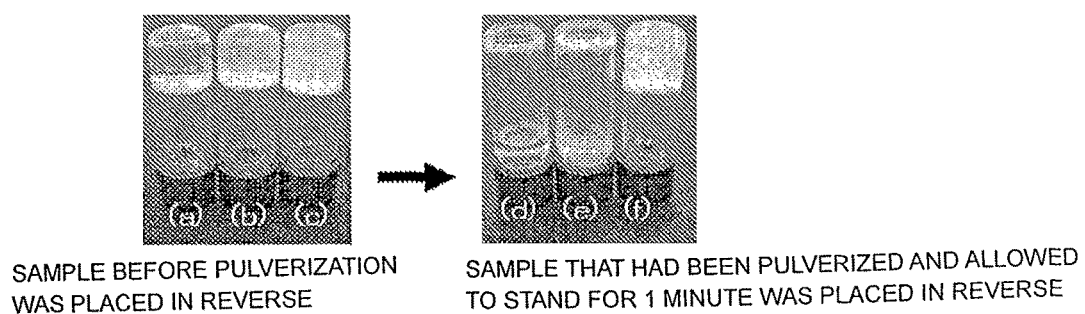

SAMPLE BEFORE PULVERIZATION
WAS PLACED IN REVERSE

SAMPLE THAT HAD BEEN PULVERIZED AND ALLOWED
TO STAND FOR 1 MINUTE WAS PLACED IN REVERSE

FIG. 14

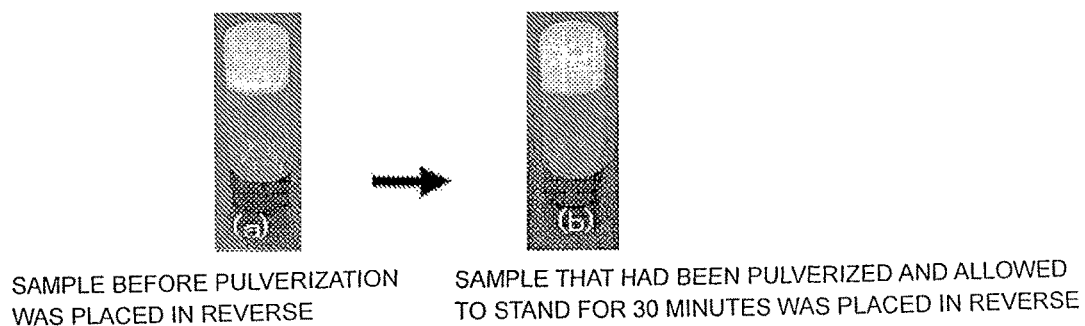

SAMPLE BEFORE PULVERIZATION
WAS PLACED IN REVERSE

SAMPLE THAT HAD BEEN PULVERIZED AND ALLOWED
TO STAND FOR 30 MINUTES WAS PLACED IN REVERSE

FIG. 17
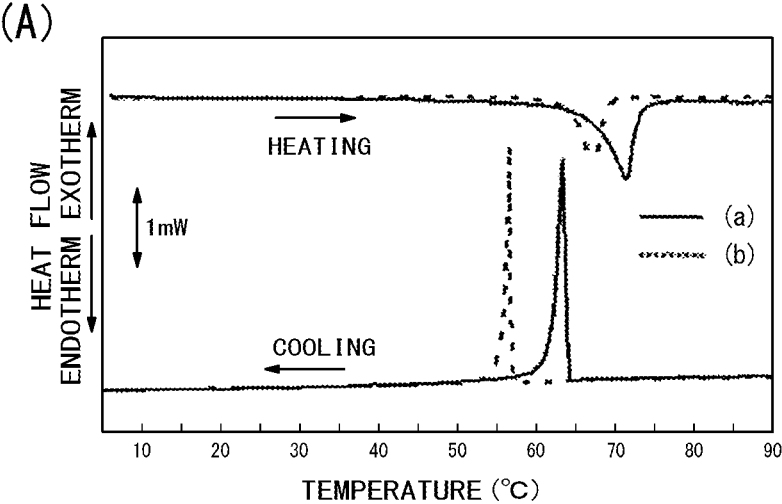
(A)
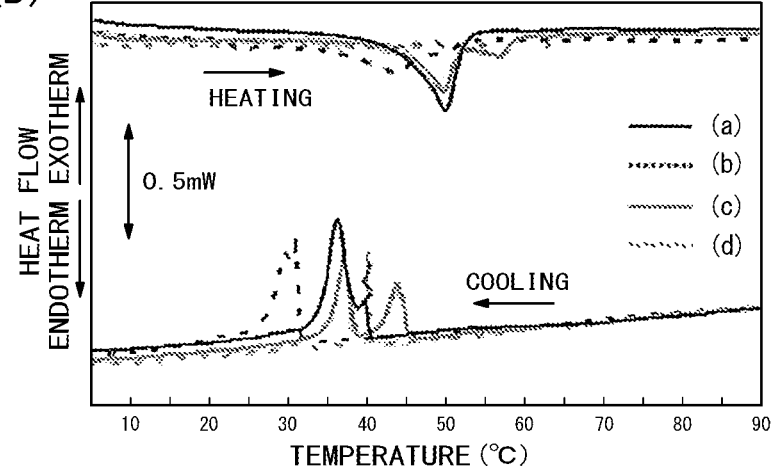
(B)

FIG. 20

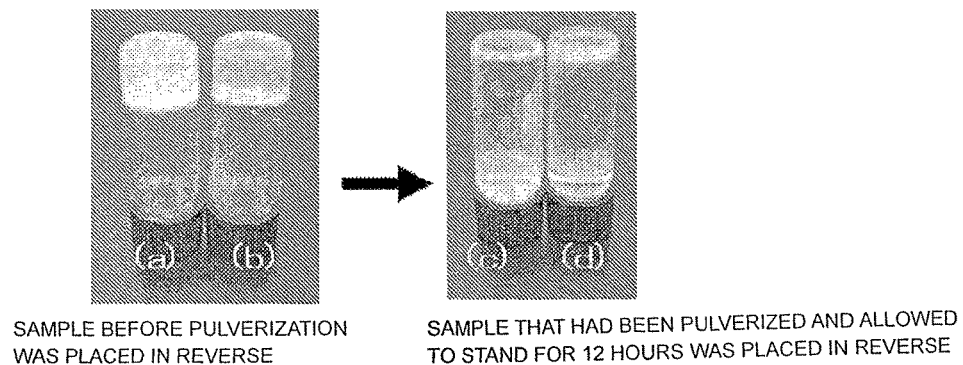

SAMPLE BEFORE PULVERIZATION WAS PLACED IN REVERSE

SAMPLE THAT HAD BEEN PULVERIZED AND ALLOWED TO STAND FOR 12 HOURS WAS PLACED IN REVERSE

FIG. 21

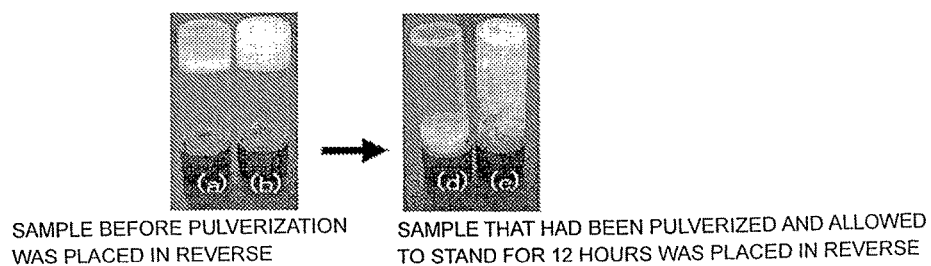

SAMPLE BEFORE PULVERIZATION WAS PLACED IN REVERSE

SAMPLE THAT HAD BEEN PULVERIZED AND ALLOWED TO STAND FOR 12 HOURS WAS PLACED IN REVERSE

FIG. 22

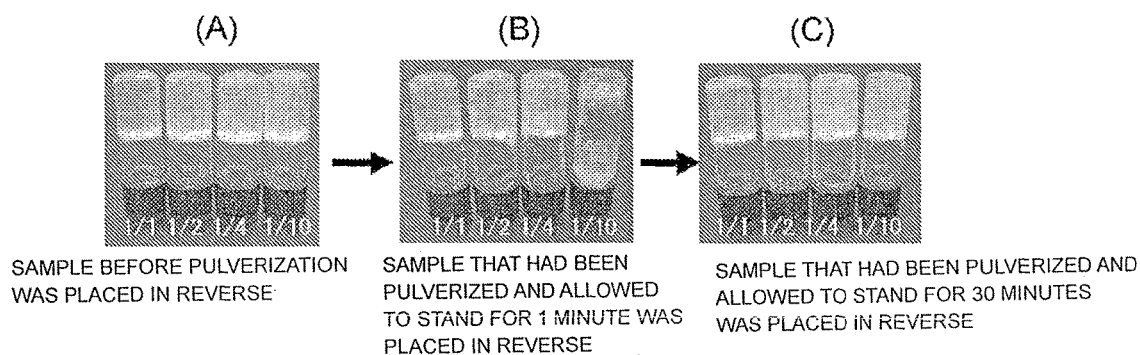

(A) SAMPLE BEFORE PULVERIZATION WAS PLACED IN REVERSE (B) SAMPLE THAT HAD BEEN PULVERIZED AND ALLOWED TO STAND FOR 1 MINUTE WAS PLACED IN REVERSE (C) SAMPLE THAT HAD BEEN PULVERIZED AND ALLOWED TO STAND FOR 30 MINUTES WAS PLACED IN REVERSE

SAMPLE BEFORE PULVERIZATION
WAS PLACED IN REVERSE

SAMPLE THAT HAD BEEN PULVERIZED AND ALLOWED
TO STAND FOR 30 MINUTES WAS PLACED IN REVERSE

FIG. 32
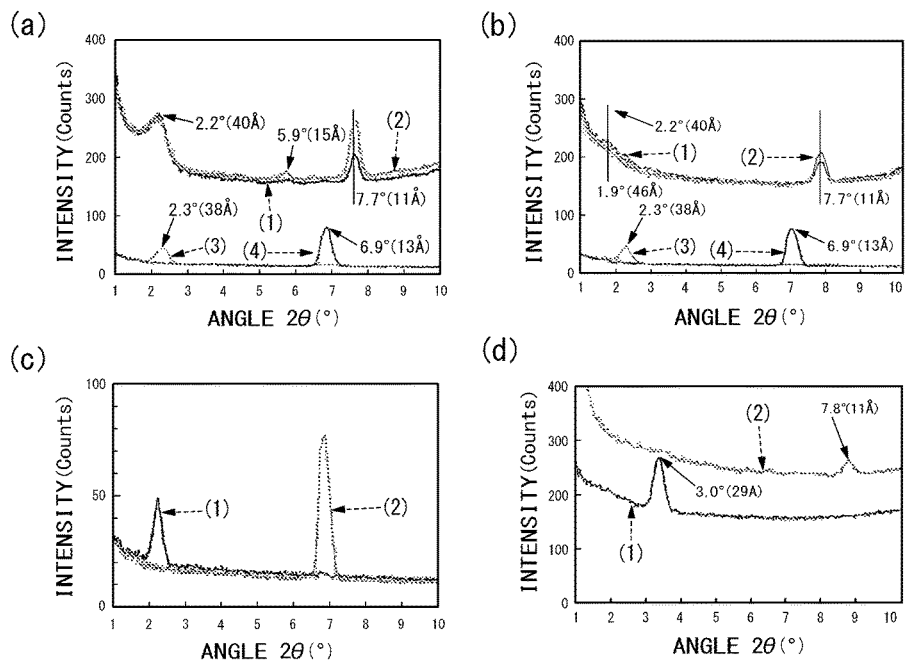
FIG. 33
(a)
C18U (OCTADECYLUREA)
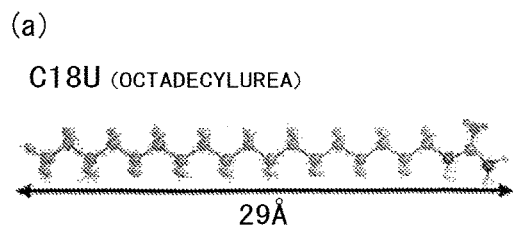
C4U (BUTYLUREA))
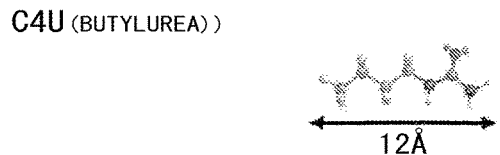
(b)
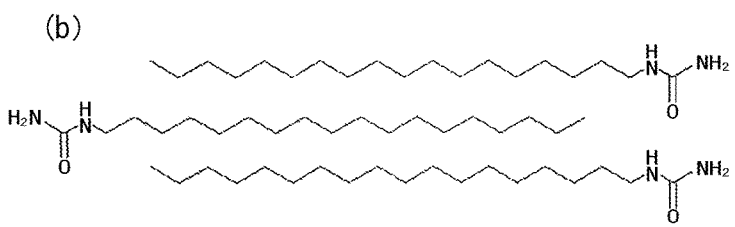

GELATOR AND ORGANOGEL

TECHNICAL FIELD

The present invention relates to a gelator comprising two or more homologous alkyl compounds, an organogel produced from the gelator, and a method for producing the organogel.

BACKGROUND ART

Organogelators (oil gelators) are used in the fields of cosmetics, pharmaceutical products, agrochemicals, foods, adhesives, paints, resins, and similar products to control the flowabilities of the products. Such a gelator can solidify organic solvents and domestic oil wastes, which cause environmental pollution, for recovery. In addition, organogels produced by such a gelator can be used as chemomechanical system materials, impact/vibration absorbers, materials for imparting sustained-release properties to pharmaceutical products, and the like, and thus the organogelators have been drawing attention. The gelators have been studied and developed mainly on polymer compounds, but in recent years, low-molecular weight compounds, which have excellent characteristics as gelators, have been being studied. Organogels formed from such a gelator are required to have appropriate strength, transparency, and continuous sol-gel conversion properties (thixotropic properties) depending on use thereof.

As described above, the organogels have been used in a wide variety of fields and are expected to be used in wider fields in future. On this account, as the application fields of the organogels expand, organogelators of low-molecular weight compounds (hereinafter also called low-molecular weight gelators) are required to have the ability to form a gel from a wide variety of organic solvents. To address these requirements, urea compounds (for example, Patent Documents 1 to 3) and amide compounds (for example, Non-Patent Document 1) are described as low-molecular weight gelators capable of forming a gel having excellent stability from various organic solvents by adding a small amount of such a compound. It is also described that an α-aminolactam derivative has the ability to form gels from squalane, a liquid paraffin, and the like (for example, Patent Document 4). However, these compounds alone fail to provide sufficient mechanical strength, thixotropic properties, or the like. Use of acrylamide is described as an amide gel capable of providing mechanical strength, but the production of such a gel necessitates polymerization reaction, and thus is complicated (for example, Patent Document 5). For a gel that is formed from an organogelator comprising a single compound but had insufficient performances, a described case can solve such a disadvantage by mixing a plurality of compounds (Patent Document 6). However, there are innumerable combinations of the compounds and the usage thereof, and the determination of the optimal combination requires much effort.

PRIOR ART DOCUMENTS

Patent Documents

Patent Document 1: Japanese Patent Application Publication No. 2000-256303 (JP 2000-256303 A)
Patent Document 2: Japanese Patent Application Publication No. 2004-359643 (JP 2004-359643 A)
Patent Document 3: Japanese Patent Application Publication No. 2010-077037 (JP 2010-077037 A)
Patent Document 4: Japanese Patent No. 3690052
Patent Document 5: Japanese Patent Application Publication No. 2010-111821 (JP 2010-111821 A)
Patent Document 6: Japanese Application Publication No. 2008-515911 (JP 2008-515911 T)

Non-Patent Document

Non-Patent Document 1: R. G Weiss et al. Langmuir, 25 (2009) 8615-8625

SUMMARY OF THE INVENTION

Problem to be Solved by the Invention

Related art organogels having high mechanical strength, transparency, and other characteristics are polymer compounds that necessitate a complicated synthesis process. Alternatively, the preparation of such organogels necessitates polymerization reaction of special low-molecular weight compounds or examination of innumerable combinations of various gelators. To address these problems, a method of producing organogels having the above-mentioned characteristics by a simpler technique has been desired.

In view of the above, it is an object of the present invention to provide a novel organogel produced by an unknown technique.

As a result of intensive studies for solving the disadvantages, the inventor of the present invention has found that a gelator produced by mixing two or more homologous alkyl compounds having different chain lengths can be suitably applied for non-aqueous solvents including organic solvents and, surprisingly, can form an organogel having higher mechanical strength and higher transparency and exhibiting thixotropic properties, and have accomplished the present invention.

Specifically, as a first aspect, the present invention relates to a gelator characterized by comprising two or more alkylamide compounds of General Formula [I]:

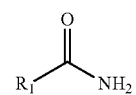

(where $R_1$ is a $C_{1-30}$ aliphatic group optionally having a substituent) or
two or more alkylurea compounds of General Formula [II]:

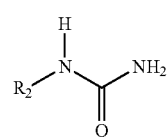

(where $R_2$ is a $C_{1-30}$ aliphatic group optionally having a substituent), characterized in that the gelator forms a gel exhibiting thixotropic properties.

As a second aspect, the present invention relates to the gelator according to the first aspect, comprising an alkylamide compound of Formula [I] where $R_1$ is a $C_{5-7}$ aliphatic group optionally having a substituent and an alkylamide compound of Formula [I] where $R_1$ is a $C_{11-21}$ aliphatic group optionally having a substituent.

As a third aspect, the present invention relates to the gelator according to the first aspect or the second aspect, comprising two alkylamide compounds where the aliphatic groups as $R_1$ have different numbers of carbon atoms, and an alkylamide compound (A) having $R_1$ with a larger number of carbon atoms and an alkylamide compound (B) having $R_1$ with a smaller number of carbon atoms are contained in a mass ratio of (A):(B)=1 to 20:20 to 1.

As a fourth aspect, the present invention relates to the gelator according to the first aspect or the second aspect, comprising three alkylamide compounds of Formula [I] where the aliphatic groups as $R_1$ have different numbers of carbon atoms, and an alkylamide compound (C) having $R_1$ with the largest number of carbon atoms, an alkylamide compound (D) having $R_1$ with a smaller number of carbon atoms than the number of carbon atoms of the alkylamide compound (C), and an alkylamide compound (E) having $R_1$ with a smaller number of carbon atoms than the number of carbon atoms of the alkylamide compound (D) are contained in a mass ratio of (C):(D):(E)=1 to 5:1 to 5:1 to 20.

As a fifth aspect, the present invention relates to the gelator according to the first aspect, comprising an alkylurea compound of Formula [II] where $R_2$ is a $C_{4-8}$ aliphatic group optionally having a substituent and an alkylurea compound of Formula [II] where $R_2$ is a $C_{12-18}$ aliphatic group optionally having a substituent.

As a sixth aspect, the present invention relates to the gelator according to the first aspect or the fifth aspect, comprising two alkylurea compounds where the aliphatic groups as $R_2$ have different numbers of carbon atoms, and an alkylurea compound (A) having $R_2$ with a larger number of carbon atoms and an alkylurea compound (B) having $R_2$ with a smaller number of carbon atoms are contained in a mass ratio of (A):(B)=1 to 20:20 to 1.

As a seventh aspect, the present invention relates to a gel comprising two or more alkylamide compounds of General Formula [I]:

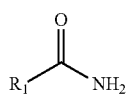

[I]

(where $R_1$ is a $C_{1-30}$ aliphatic group optionally having a substituent) or two or more alkylurea compounds of General Formula [II]:

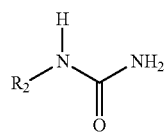

[II]

(where $R_2$ is a $C_{1-30}$ aliphatic group optionally having a substituent), characterized in that the gel exhibits thixotropic properties.

Effects of the Invention

The gelator of the present invention enables gelation of an organic solvent to form a gel by a simple technique.

In particular, the gelator of the present invention enables the formation of organogels of various organic solvents having various dielectric constants, and the resulting organogels have high mechanical strength, high transparency, and thixotropic properties.

BRIEF DESCRIPTION OF THE DRAWINGS

[FIG. 1A: stearic acid amide; FIG. 1B: octadecylamide; FIG. 1C: n-octanamide; the parenthesized numeric characters represent concentrations of the derivatives; solvents used: (a), (l), (w) propylene carbonate; (b), (m) N,N-dimethylformamide; (c), (n) methanol; (d), (o) ethanol; (e), (p) n-butanol; (f), (q), (x) 1,2-dichloroethane; (g), (r) tetrahydrofuran; (h), (s), (y) ethyl acetate; (i), (t), (z) SH245; (j), (u), (A) toluene; (k), (v), (B) n-octane].

[FIG. 2A: octadecylurea; FIG. 2B: butylurea; the parenthesized numeric characters represent concentrations of the derivatives; solvents used: (a), (l) propylene carbonate; (b) N,N-dimethylformamide; (c) methanol; (d) ethanol; (e) n-butanol; (0, (m) 1,2-dichloroethane; (g) tetrahydrofuran; (h) ethyl acetate; (i) SH245; (j), (n) toluene; (k) n-octane].

FIG. 3A: stearic acid amide, FIG. 3B: hexadecanamide, FIG. 3C: n-octanamide, FIG. 3D: erucic acid amide, FIG. 3E: behenic acid amide; alkylurea derivatives: FIG. 3F: octadecylurea, FIG. 3G: butylurea; the parenthesized numeric characters represent concentrations of the derivatives; fixed oil used: (a) olive oil; (b) squalane; (c) isopropyl myristate].

FIG. 4B: a toluene gel with 4 wt % stearic acid amide/hexadecanamide; FIG. 4C: a toluene gel with 4 wt % hexadecanamide/n-octanamide; the numeric characters in the figures represent mixing ratios in terms of mass).

[FIG. 6A: (a) a toluene gel with 3 wt % stearic acid amide, (b) a toluene gel with 6 wt % hexadecanamide, (c) a toluene gel with 3 wt % n-octanamide; FIG. 6B: (a) a toluene gel with 4 wt % stearic acid amide/hexadecanamide/n-octanamide at a mixing ratio of 1/1/2 in terms of mass, (b) a toluene gel with 4 wt % stearic acid amide/hexadecanamide/n-octanamide at a mixing ratio of 1/1/4 in terms of mass, (c) a toluene gel with 4 wt % stearic acid amide/hexadecanamide/n-octanamide at a mixing ratio of 1/1/10 in terms of mass].

[FIG. 7A: frequency dependence test results; (a) a toluene gel with 3 wt % stearic acid amide, (b) a toluene gel with 6 wt % hexadecanamide, (c) a toluene gel with 3 wt % n-octanamide; FIG. 7B: strain dependence test results: (a) a toluene gel with 3 wt % stearic acid amide, (b) a toluene gel with 6 wt % hexadecanamide, (c) a toluene gel with 3 wt % n-octanamide].

FIG. 8 includes views showing evaluation results of viscoelastic characteristics of gels with a mixture of three alkylamide derivatives in Example 7 [FIG. 8A: frequency dependence test result: (a) a toluene gel with 4 wt % stearic acid amide/hexadecanamide/n-octanamide at a mixing ratio of 1/1/2 in terms of mass, (b) a toluene gel with 4 wt % stearic acid amide/hexadecanamide/n-octanamide at a mixing ratio of 1/1/4 in terms of mass, (c) a toluene gel with 4 wt % stearic acid amide/hexadecanamide/n-octanamide a mixing ratio of 1/1/10 in terms of mass; FIG. 8B: strain dependence test results: (a) a toluene gel with 4 wt % stearic acid amide/hexadecanamide/n-octanamide at a mixing ratio of 1/1/2 in terms of mass, (b) a toluene gel with 4 wt % stearic acid amide/hexadecanamide/n-octanamide at a mixing ratio of 1/1/4 in terms of mass, (c) a toluene gel with 4 wt % stearic acid amide/hexadecanamide/n-octanamide at a mixing ratio of 1/1/10 in terms of mass].

FIG. 9 includes photographs showing gelation behavior ((a) to (c): reversed samples before pulverization) and thixotropic behavior ((d) to (f): reversed samples that were allowed to stand for 12 hours after pulverization) of toluene solutions of various alkylamide derivatives (single component) in Example 8 ((a) and (d) a toluene gel with 3 wt % stearic acid amide, (b) and (e) a toluene gel with 6 wt % hexadecanamide, (c) and (f) a toluene gel with 3 wt % n-octanamide).

FIG. 10 includes photographs showing gelation behavior ((a) to (c): reversed samples before pulverization) and thixotropic behavior ((d) to (f): reversed samples that were allowed to stand for 1 minute after pulverization, (g) to (i): reversed samples that were allowed to stand for 5 minutes after pulverization) of toluene solutions of 4 wt % mixture of alkylamide derivatives (mixture of three components) in Example 9 ((a), (d), (g) the mixing ratio of stearic acid amide/hexadecanamide/n-octanamide is 1/1/2 in terms of mass, (b), (e), (h) the mixing ratio is 1/1/4 in terms of mass, (c), (f), (i) the mixing ratio is 1/1/10 in terms of mass).

FIG. 11 includes photographs showing gelation behavior ((a) to (c): reversed samples before pulverization) and thixotropic behavior ((d) to (f): reversed samples that were allowed to stand for 12 hours after pulverization) of squalane with alkylamide derivatives (single component) at a minimum gelation concentration in Example 9 ((a), (d) a gel with 2 wt % stearic acid amide, (b), (e) a gel with 2 wt % hexadecanamide, (c), (f) a gel with 1 wt % n-octanamide).

FIG. 12 includes photographs showing gelation behavior ((a) and (b): reversed samples before pulverization) and thixotropic behavior ((c) and (d): reversed samples that were allowed to stand for 12 hours after pulverization) of gels of squalane with alkylamide derivatives (single component) at a minimum gelation concentration in Example 9 ((a), (c) 2 wt % erucic acid amide, (b), (d) 2 wt % behenic acid amide).

FIG. 13 includes photographs showing gelation behavior ((a) to (c): reversed samples before pulverization) and thixotropic behavior ((d) to (f): reversed samples that were allowed to stand for 1 minute after pulverization) of gels of a fixed oil mixed with three alkylamide derivatives (squalane gels with 1 wt % stearic acid amide/hexadecanamide/n-octanamide at a mixing ratio of 1/1/10 in terms of mass) in Example 10 ((a), (d) a concentration of 0.5 wt %, (b), (e) a concentration of 1.0 wt %, (c), (f) a concentration of 2.0 wt %).

FIG. 14 includes photographs showing gelation behavior ((a): reversed samples before pulverization) and thixotropic behavior ((b): reversed sample that was allowed to stand for 30 minutes after pulverization) of a gel of a fixed oil mixed with two alkylamide derivatives (squalane gels with 1 wt % erucic acid amide/behenic acid amide at a mixing ratio of 1/1 in terms of mass) in Example 10.

FIG. 17 includes views showing differential scanning calorimetry results of gels with a single alkylurea derivative and toluene gels with a mixture of two alkylurea derivatives at various mixing ratios in Example 14 [FIG. 17A: (a) a toluene gel with 2 wt % octadecylurea, (b) a toluene gel with 6 wt % butylurea; FIG. 17B: (a) a toluene gel with 3 wt % octadecylurea/butylurea at a mixing ratio of 1/1 in terms of mass, (b) a toluene gel with 3 wt % octadecylurea/butylurea at a mixing ratio of 1/2 in terms of mass, (c) a toluene gel with 3 wt % octadecylurea/butylurea at a mixing ratio of 1/4 in terms of mass, (d) a toluene gel with 3 wt % octadecylurea/butylurea at a mixing ratio of 1/10 in terms of mass].

[FIG. 18A: frequency dependence test results; (a) a toluene gel with 2 wt % octadecylurea, (b) a toluene gel with 6 wt % butylurea; FIG. 18B: strain dependence test results; (a) a toluene gel with 2 wt % octadecylurea, (b) a toluene gel with 6 wt % butylurea].

[FIG. 19A: frequency dependence test results; (a) a toluene gel with 3 wt % octadecylurea/butylurea at a mixing ratio of 1/1 in terms of mass, (b) a toluene gel with 3 wt % octadecylurea/butylurea at a mixing ratio of 1/2 in terms of mass; FIG. 19B: strain dependence test results; (a) a toluene gel with 3 wt % octadecylurea/butylurea at a mixing ratio of 1/1 in terms of mass, (b) a toluene gel with 3 wt % octadecylurea/butylurea at a mixing ratio of 1/2 in terms of mass; FIG. 19C: frequency dependence test results; (c) a toluene gel with 3 wt % octadecylurea/butylurea at a mixing ratio of 1/4 in terms of mass, (d) a toluene gel with 3 wt % octadecylurea/butylurea at a mixing ratio of 1/10 in terms of mass; FIG. 19D: strain dependence test results; (c) a toluene gel with 3 wt % octadecylurea/butylurea at a mixing ratio of 1/4 in terms of mass, (d) a toluene gel with 3 wt % octadecylurea/butylurea at a mixing ratio of 1/10 in terms of mass].

FIG. 20 includes photographs showing gelation behavior ((a), (b): reversed samples before pulverization) and thixotropic behavior ((c), (d): reversed samples that was allowed to stand for 12 hours after pulverization) of toluene solutions of various alkylurea derivatives (single component) in Example 16 ((a) and (c) a toluene gel with 3 wt % octadecylurea, (b) and (d) a toluene gel with 6 wt % butylurea).

FIG. 21 includes photographs showing gelation behavior ((a), (b): reversed samples before pulverization) and thixotropic behavior ((c), (d): reversed samples that was allowed to stand for 12 hours after pulverization) of isopropyl myristate solutions of various alkylurea derivatives (single component) in Example 16 ((a) and (c) an isopropyl myristate gel with 1 wt % octadecylurea; (b) and (d) an isopropyl myristate gel with 1 wt % butylurea).

FIG. 22 includes photographs showing gelation behavior (FIG. 22A: reversed samples before pulverization) and thixotropic behavior (FIG. 22B: reversed samples that was allowed to stand for 1 minute after pulverization, FIG. 22C: reversed samples that were allowed to stand for 30 minutes after pulverization) of toluene solutions of 3 wt % various alkylurea derivatives (mixture of two components) in Example 16 (the numeric characters in the figures represent mixing ratios of octadecylurea/butylurea in terms of mass).

FIG. 30B: (1) a crystal sample of stearic acid amide, (2) a crystal sample of hexadecanamide, (3) a crystal sample of n-octanamide, (4) a toluene gel with 3 wt % stearic acid amide, (5) a toluene gel with 6 wt % hexadecanamide, (6) a toluene gel with 3 wt % n-octanamide).

FIG. 32 includes views showing the results of X-ray diffraction analysis in a small angle region of toluene gels of a single alkylurea derivative, toluene gels with a mixture of three alkylurea derivatives, and crystals of alkylurea derivatives in Example 22 (FIG. 32A: (1) a toluene gel with 3 wt % octadecylurea/butylurea at a mixing ratio of 1/1 in terms of mass, (2) a toluene gel with 3 wt % octadecylurea/butylurea at a mixing ratio of 1/2 in terms of mass, (3) a crystal sample of octadecylurea, (4) a crystal sample of butylurea; FIG. 32B: (1) a toluene gel with 3 wt % octadecylurea/butylurea at a mixing ratio of 1/4 in terms of mass, (2) a toluene gel with 3 wt % octadecylurea/butylurea at a mixing ratio of 1/10 in terms of mass, (3) a crystal sample of octadecylurea, (4) a crystal sample of butylurea; FIG. 32C: (1) a crystal sample of octadecylurea, (2) a crystal sample of butylurea; FIG. 32D: (1) a toluene gel with 2 wt % octadecylurea, (2) a toluene gel with 6 wt % butylurea).

FIG. 33A is a view showing molecular models (the molecular length is calculated by ChemDraw3D and includes van der Waals radii of two amino groups and two methyl groups; the van der Waals radii are according to literatures (J. Phys. Chem., (1964), vol. 68, p. 441-451 and J. Phys. Chem., (1996), vol. 100, p. 7384-7391) of alkylurea derivatives (octadecylurea, butylurea) and dimers configured so as to form hydrogen bonds. FIG. 33B is a view showing a lamella structure which the alkylamide derivatives can form.

MODES FOR CARRYING OUT THE INVENTION

Figure 1:
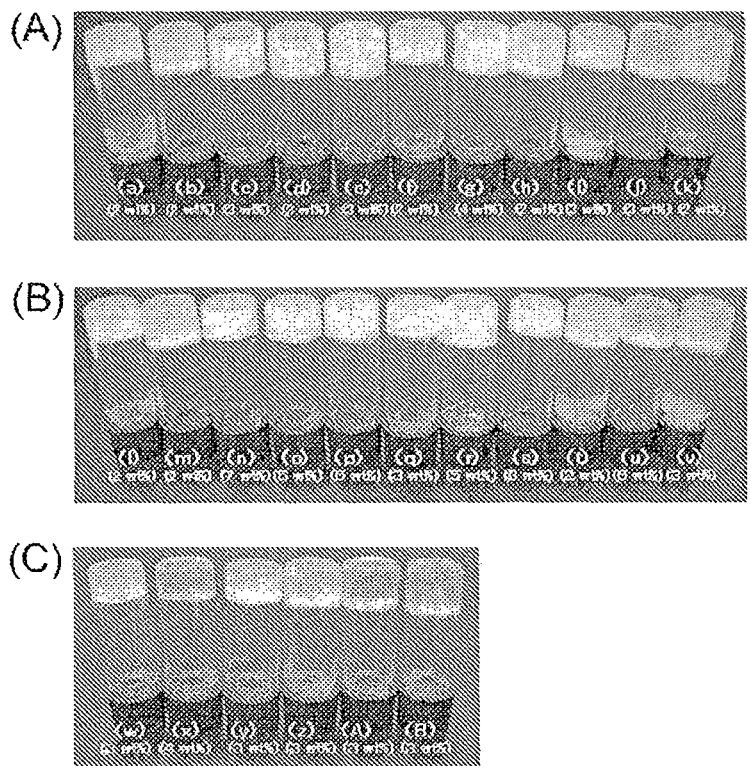
FIG. 1 includes photographs showing gelation behavior of various solutions of alkylamide derivatives in Comparative Example 1 to Comparative Example 3

The present invention relates to a gelator comprising two or more alkylamide compounds of General Formula [I] or two or more alkylurea compounds of General Formula [II].

The present invention will now be described in detail. Hereinafter, "compound of General Formula [I]" is also called "compound [I]". Other compounds with the formula numbers are expressed similarly. "Alkylamide compounds" and "alkylurea compounds" are also called "alkylamide derivatives" and "alkylurea derivatives", respectively.

In the definitions of $R_1$ in General Formula [I] and $R_2$ in General Formula [II], the aliphatic group is preferably a $C_{1-30}$ alkyl group, is exemplified by linear or branched alkyl groups having a carbon atom number of 1 to 30 and cyclic alkyl groups having a carbon atom number of 3 to 30, and is preferably a linear, branched, or cyclic alkyl group having a carbon atom number of 5 to 22.

Specific examples of the aliphatic group include the following linear, branched, or cyclic pentyl groups, hexyl groups, heptyl groups, octyl groups, nonyl groups, decyl groups, undecyl groups, dodecyl groups (lauryl groups), tridecyl groups, tetradecyl groups (myristyl groups), pentadecyl groups, hexadecyl groups (cetyl groups, palmityl groups), heptadecyl groups (margaryl groups), octadecyl groups (stearyl groups), nonadecyl groups, icosyl groups, eicosyl groups, and henicosyl groups.

Specifically, $R_1$ is preferably $C_{5-7}$ alkyl groups and $C_{11-21}$ alkyl groups and particularly preferably an n-heptyl group, an n-pentadecyl group, and an n-heptadecyl group. $R_2$ is preferably $C_{4-8}$ alkyl groups and $C_{12-18}$ alkyl groups and particularly preferably an n-butyl group and an n-octadecyl group.

The alkyl group may have one to three substituents that may be the same or different. Examples of the substituent include a hydroxy group, a carboxy group, halogen atoms, alkoxy groups, alkoxyalkoxy groups, and fluorine-substituted alkoxy groups.

The alkyl moiety of the alkoxy group is exemplified by linear or branched alkyl groups having a carbon atom number of 1 to 8 and cyclic alkyl groups having a carbon atom number of 3 to 8. Specific examples of the alkyl moiety include a methyl group, an ethyl group, a propyl group, an isopropyl group, a butyl group, an isobutyl group, a sec-butyl group, a tert-butyl group, a pentyl group, an isopentyl group, a 2-methylbutyl group, a tert-pentyl group, a hexyl group, an octyl group, a cyclopropyl group, a cyclobutyl group, a cyclopentyl group, a cyclohexyl group, a cycloheptyl group, and a cyclooctyl group. The fluorine-substituted alkoxy group is exemplified by groups prepared by substituting at least one hydrogen of the alkyl moiety of the alkoxy group with a fluorine atom.

Examples of the halogen atom include a fluorine atom, a chlorine atom, a bromine atom, and an iodine atom.

The definition of the alkyl moiety of the alkoxyalkoxy group (—O-alkylene-O-alkyl group) is the same as above, and the alkylene moiety of the alkoxyalkoxy group is the same as the alkyl group from which a hydrogen atom is eliminated.

The alkyl group may include one or more unsaturated double bonds or unsaturated triple bonds, and the alkyl group may be interrupted by an oxygen atom or a nitrogen atom.

The gelator of the present invention is prepared by mixing two or more compounds [I] or two or more compounds [II] and is used as a gelator.

For example, the gelator can be a mixture of two or three of n-octanamide as a compound [I] where $R_1$ is a heptyl group, hexadecanamide as a compound [I] where $R_1$ is a pentadecyl group, and stearic acid amide as a compound [I] where $R_1$ is a heptadecyl group. Specifically, the mixture of two compounds can be a mixture of stearic acid amide and hexadecanamide at a mass ratio of 20 to 1:1 to 20, preferably at a ratio of 10 to 1:1 to 10, more preferably at a ratio of 10 to 1:1 to 1. In addition, the mixture can be a mixture of stearic acid amide and n-octanamide at a mass ratio of 20 to 1:1 to 20, preferably at a ratio of 10 to 1:1 to 10, and can be a mixture of hexadecanamide and n-octanamide at a mass ratio of 20 to 1:1 to 20, preferably at a ratio of 10 to 1:1 to 10. The mixture of three compounds can be specifically a mixture of stearic acid amide, hexadecanamide, and n-octanamide at a mass ratio of 1 to 20:1 to 20:1 to 20, preferably at a ratio of 1 to 5:1 to 5:1 to 20.

Alternatively, the gelator can be a mixture of butylurea as a compound [II] where $R_2$ is a butyl group and octadecylurea as a compound [II] where $R_2$ is an octadecyl group as the mixture of two compounds. For example, the mixture of two compounds can be a mixture of octadecylurea and butylurea at a mass ratio of 20 to 1:1 to 20, preferably at a ratio of 10 to 1:1 to 10, more preferably at a ratio of 10 to 1:1 to 5.

The gelator of the present invention comprising a mixture of these two or more compounds can be used in a smaller amount than that of a gelator comprising a single compound and enables gelation of an organic solvent as a medium. In addition, the gelator enables gelation of an organic solvent that cannot form a gel with a single compound.

The gelator comprising a mixture of these two or more compounds enables the formation of a gel having thixotropic properties, high mechanical strength, and high transparency.

Examples of the organic solvent that forms a gel in the present invention include aromatic hydrocarbon solvents such as benzene, toluene, xylene, ethylbenzene, and tetralin; aliphatic or alicyclic hydrocarbon solvents such as n-hexane, n-heptane, n-octane, mineral spirits, and cyclohexane; halogenated solvents such as methyl chloride, methyl bromide, methyl iodide, methylene dichloride, chloroform, carbon tetrachloride, dichloroethane, trichloroethylene, perchloroethylene, and ortho-dichlorobenzene; ester or ester ether solvents such as ethyl acetate, butyl acetate, methoxybutyl acetate, methyl cellosolve acetate, ethyl cellosolve acetate, γ-butyrolactone, γ-valerolactone, and propylene glycol monomethyl ether acetate; ether solvents such as diethyl ether, tetrahydrofuran, 1,4-dioxane, methyl cellosolve, ethyl cellosolve, butyl cellosolve, propylene glycol monomethyl ether, and 1,2-dimethoxyethane; ketone solvents such as acetone, methyl ethyl ketone, methyl isobutyl ketone, di-n-butyl ketone, and cyclohexanone; alcoholic solvents such as methanol, ethanol, n-propanol, isopropanol (2-propanol), n-butanol, isobutanol, tert-butanol, 2-ethylhexyl alcohol, benzyl alcohol, and ethylene glycol; chain or cyclic carbonates such as dimethyl carbonate (DMC), diethyl carbonate (DEC), ethyl methyl carbonate, ethylene carbonate, propylene carbonate, and vinylene carbonate; amide solvents such as N,N-dimethylformamide (DMF) and N,N-dimethylacetamide; sulfoxide solvents such as dimethyl sulfoxide (DMSO); heterocyclic compound solvents such as N-methyl-2-pyrrolidone; nitrile solvents such as acetonitrile; silicone solvents such as cyclic siloxane; and mixed solvents of two or more of them.

The gelator of the present invention is preferably used in such an amount that the total amount of two or more alkylurea compounds or two or more alkylurea compounds is 0.1 to 30% by mass, preferably 0.5 to 20% by mass, and more preferably 1 to 10% by mass relative to an organic solvent as the medium.

The gelator of the present invention is added to an organic solvent as the medium. The mixture is heated and stirred to be dissolved, as necessary, and is allowed to stand at room temperature, giving a gel. The strength of the gel can be adjusted by the concentration of the gelator.

The gel formed with the gelator of the present invention may contain various additives (including organic compounds such as surfactants, ultraviolet absorbers, moisturizers, antiseptics, antioxidants, aromatics, and physiologically active substances (medical components) and inorganic compounds such as titanium oxide, talc, mica, and water) depending on applications and purposes, as necessary, to such an extent that the gel forming ability of the gelator is not impaired.

A gel comprising two or more compounds [I] or two or more compounds [II] that are the gelator of the present invention and a gel comprising a mixture of two or more compounds [I] or two or more compounds [II] and exhibiting thixotropic properties are also included in the present invention.

EXAMPLES

The present invention will next be described in further detail with reference to examples, but the present invention is not limited to the following examples.

The reagents described in the following examples were purchased from Tokyo Chemical Industry Co., Ltd., and the solvents were purchased from Wako Pure Chemical Industries, Ltd., and were used as they were. Specifically, the materials are stearic acid amide (90%), hexadecanamide (95%), n-octanamide (98%), octadecylurea (97%), butylurea (96%), erucic acid amide (85%), and behenic acid amide (75%).

Apparatuses and conditions used for various measurements and analyses are shown below.
(1) Transmittance measurement
* HR4000 spectrometer, manufactured by Ocean Photonics Inc.
* A sample was placed in a quartz cell with an optical path length of 10 mm and measured.
(2) Thixotropic property test (gel pulverization)
* Apparatus: Vortex mixer (Genie 2), manufactured by AS ONE Corporation
(3) Differential scanning calorimetry
* Apparatus: EXSTAR6000 thermal analyzer, manufactured by Hitachi High-Tech Science Corporation
* Container used: a sealable silver sample container
* Rate of temperature rise and drop: 2° C./min
(4) Evaluation of viscoelasticity and thixotropic properties of gels
* MCR-301, manufactured by Anton Paar Japan K.K.
* Measurement conditions: measurement jigs were parallel plates with a diameter of 8 mm; a gap of 0.50 mm; a measurement temperature of 25° C.; an excess gel was wiped off before measurement.
* Frequency dependence measurement: measured at a constant strain of 0.01%
* Strain dependence measurement: measured at a constant angular frequency (1 rad/sec)
* Evaluation of thixotropic properties: a low shear (strain amplitude of 0.01%, a frequency of 1 Hz) and a high shear (a shear velocity of 3,000 sec$^{-1}$ was applied for 0.1 second) were repeatedly applied, and changes in elastic modulus were determined.
(5) Optical microscope observation
* Leica DM2500, Leica Microsystems
(6) Scanning electron micrograph
* Apparatus: SU-8000, manufactured by Hitachi High-Technologies Corporation
* Acceleration voltage: 1.0 kV
* Sample treatment: samples were treated with an electrically conductive substance (Pt) (a Pt film thickness of 10 nm).
(7) X-ray diffraction analysis
* D8 DISCOVER X-ray diffractometer for multifunctional thin film evaluation, manufactured by Bruker AXS
* A sample was placed in a glass capillary having a diameter of 1 mm and measured at 26° C. with a CuK α-ray.

Comparative Example 1 to Comparative Example 12: Gelation Test of Alkylamide Derivative and Alkylurea Derivative (Single Component)

In a 4-ml sample tube, an alkylamide derivative or an alkylurea derivative was placed and an organic solvent (propylene carbonate, N,N-dimethylformamide (DMF), methanol, ethanol, n-butanol, dichloroethane, tetrahydrofuran, ethyl acetate, SH245 (a cyclic silicone, decamethylcyclopentasiloxane, manufactured by Dow Corning Toray Silicone Co., Ltd.), toluene, or n-octane) was further placed in such an amount that the amount of the derivative would be a predetermined percent by mass (wt %). The sample tube was covered with a cap and was heated at 100° C. for an organic solvent having a boiling point of higher than 100° C. or at a temperature 5° C. lower than the boiling point of an organic solvent having a boiling point of 100° C. or lower, giving a solution of the alkylamide derivative or a solution of the alkylurea derivative. The solutions were allowed to cool at room temperature (about 25° C.), and the gelation was examined. After the cooling, a state where the solution had no flowability and did not run off even when the sample tube was placed in reverse was determined as "gelated".

The gelation test was carried out with solutions of various alkylamide derivatives (stearic acid amide, hexadecanamide, or n-octanamide) and alkylurea derivatives (octadecylurea or butylurea) at various concentrations, giving minimum concentrations (wt %) required for the gelation of the alkylamide derivatives and the alkylurea derivatives as minimum gelation concentrations. The state of the gel formed was also observed.

In addition, the gelation of fixed oils (olive oil, squalane, and isopropyl myristate) was similarly examined.

Figure 2:
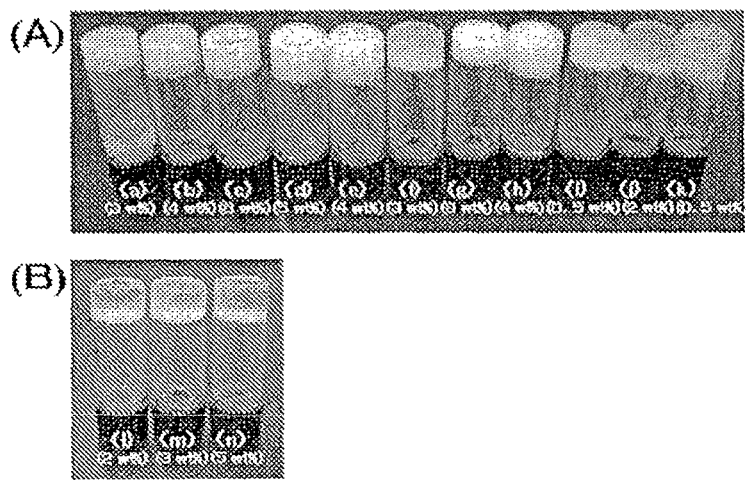
FIG. 2 includes photographs showing gelation behavior of various solutions of alkylurea derivatives in Comparative Example 4 and Comparative Example 5
Figure 3:
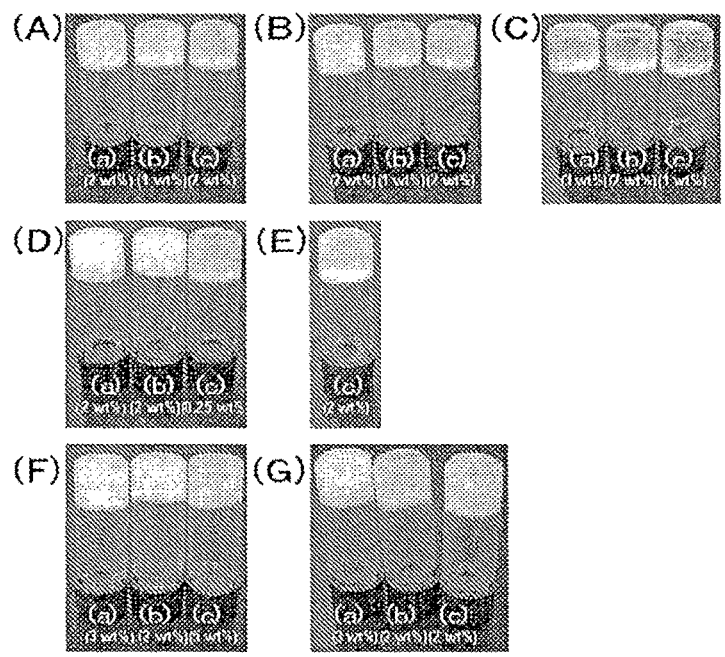
FIG. 3 includes photographs showing gelation behavior of various fixed oils with alkylamide derivatives or alkylurea derivatives in Comparative Example 6 to Comparative Example 12 [alkylamide derivatives.

The obtained results are listed in Table 1 (alkylamide derivatives), Table 2 (alkylurea derivatives), and Table 3 (fixed oils with alkylamide derivatives and alkylurea derivatives). Photographs of the sample tubes examined with various organic solvents after cooling (photographs of gels formed at minimum gelation concentrations, except solutions that failed to form gels) are shown in FIG. 1 (alkylamide derivatives: FIG. 1A: stearic acid amide, FIG. 1B:

hexadecanamide, FIG. 1C: n-octanamide), FIG. 2 (alkylurea derivatives: FIG. 2A: octadecylurea, FIG. 2B: butylurea) and FIG. 3 (alkylamide derivatives: FIG. 3A: stearic acid amide, FIG. 3B: hexadecanamide, FIG. 3C: n-octanamide, FIG. 3D: erucic acid amide, FIG. 3E: behenic acid amide; alkylurea derivatives: FIG. 3F: octadecylurea, FIG. 3G butylurea).

TABLE 1

Gelation test of various solvents with alkylamide derivatives (minimum gelation concentration: wt %)

| Organic solvent | Comparative Example 1 Stearic acid amide | Comparative Example 2 Hexa-decanamide | Comparative Example 3 n-Octa-namide | (Reference) Relative dielectric constant of organic solvent* |
|---|---|---|---|---|
| Propylene carbonate | 2.0(TG) | 2.0(TG) | 3.0(CG) | 66.14 |
| DMF | 2.0(TG) | 2.0(TG) | S | 47.24 |
| Methanol | 3.0(TG) | 7.0(TG) | S | 33.0 |
| Ethanol | 3.0(OG) | 6.0(OG) | S | 25.3 |
| n-Butanol | 3.0(OG) | 6.0(OG) | S | 17.84 |
| Dichloroethane | 2.0(TG) | 3.0(TG) | 4.0(CG) | 10.42 |
| Tetrahydrofuran | 4.0(TG) | 5.0(TG) | S | 7.52 |
| Ethyl acetate | 2.0(TG) | 8.0(TG) | 3.0(TG) | 6.0814 |
| SH245** | 3.0(TG) | 2.0(TG) | 3.0(CG) | 2.50 |
| Toluene | 3.0(TG) | 6.0(TG) | 3.0(CG) | 2.379 |
| n-Octane | 2.0(TG) | 3.0(TG) | 3.0(CG) | 1.948 |

*From "CRC Handbook of Chemistry and Physics", CRC Press, (2004), 6-155 to 6-177.
**Cyclic silicone (decamethylcyclopentasiloxane) manufactured by Dow Corning Toray Silicone Co., Ltd.
Symbols in Table:
S: solution state at 10 wt % (failed to form a gel),
TG: translucent gel (cloudy but optically transparent gel),
OG: opaque gel (cloudy gel without optical transparency),
CG: clear gel

TABLE 2

Gelation test of various solvents with alkylurea derivatives (minimum gelation concentration: wt %)

| Organic solvent | Comparative Example 4 Octadecylurea | Comparative Example 5 Butylurea | (Reference) Relative dielectric constant of organic solvent* |
|---|---|---|---|
| Propylene carbonate | 3.0(OG) | 2.0(CG) | 66.14 |
| DMF | 4.0(OG) | S | 47.24 |
| Methanol | 6.0(OG) | S | 33.0 |
| Ethanol | 5.0(OG) | S | 25.3 |
| n-Butanol | 4.0(OG) | S | 17.84 |
| 1,2-dichloroethane | 3.0(TG) | 3.0(CG) | 10.42 |
| Tetrahydrofuran | 8.0(TG) | S | 7.52 |
| Ethyl acetate | 4.0(TG) | S | 6.0814 |
| SH245** | 0.5(TG) | S | 2.50 |
| Toluene | 2.0(TG) | 5.0(CG) | 2.379 |
| n-Octane | 0.5(TG) | S | 1.948 |

*From "CRC Handbook of Chemistry and Physics", CRC Press, (2004), 6-155 to 6-177.
**Cyclic silicone (decamethylcyclopentasiloxane) manufactured by Dow Corning Toray Silicone Co., Ltd.
Symbols in Table:
S: solution state at 10 wt % (failed to form a gel),
TG: translucent gel (cloudy but optically transparent gel),
OG: opaque gel (cloudy gel without optical transparency),
CG: clear gel

TABLE 3

Gelation test of various fixed oils with various derivatives (minimum gelation concentration: wt %)

| | Various derivatives | Olive oil | Squalane | Isopropyl myristate |
|---|---|---|---|---|
| Comparative Example 6 | Stearic acid amide | 1.0(TG) | 2.0(TG) | 2.0(TG) |
| Comparative Example 7 | Hexadecanamide | 1.0(TG) | 2.0(TG) | 2.0(TG) |
| Comparative Example 8 | n-Octanamide | 2.0(CG) | 1.0(CG) | 3.0(CG) |
| Comparative Example 9 | Octadecylurea | 2.0(OG) | 0.25(OG) | 2.0(TG) |
| Comparative Example 10 | Butylurea | PG | K | 2.0(TG) |
| Comparative Example 11 | Erucic acid amide | 2.0(OG) | 1.0(OG) | 3.0(TG) |
| Comparative Example 12 | Behenic acid amide | 2.0(OG) | 2.0(OG) | 3.0(OG) |

Symbols in Table:
K: crystal precipitation at 10 wt % (failed to form a gel),
PG: partial gel at 10 wt % (failed to form a gel),
TG: translucent gel (cloudy but optically transparent gel),
OG: opaque gel (cloudy gel without optical transparency),
CG: clear gel As shown by the results in Table 1, 2, and 3, FIGS. 1, 2, and 3, the alkylamide derivatives and the alkylurea derivatives have the ability to form a gel from various organic solvents having various relative dielectric constants and various fixed oils.

Example 1: Gelation Test of Mixture of Alkylamide Derivatives 1

Figure 4:
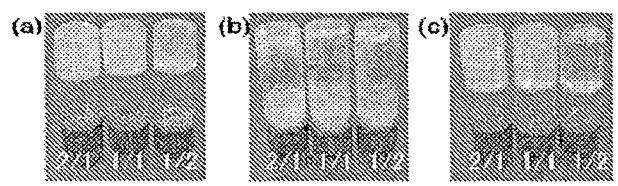
FIG. 4 includes photographs showing gelation behavior of toluene solutions of mixtures of two alkylamide derivatives at various mixing ratios in Example 1 (FIG. 4A: a toluene gel with 4 wt % stearic acid amide/n-octanamide.

Toluene solutions of a mixture of two alkylamide derivatives were subjected to the gelation test in the same procedure as in Comparative Examples 1 to 3. Toluene solutions of stearic acid amide/hexadecanamide, stearic acid amide/n-octanamide, and hexadecanamide/n-octanamide were prepared at various mixing ratios and concentrations (see Table 4 to Table 6, the concentration was a concentration of the mixture) and were subjected to the gelation test. Table 4 to Table 6 list the observation results. Photographs of the sample tubes examined with the toluene solutions after cooling are shown in FIG. 4 [FIG. 4A stearic acid amide/n-octanamide at a concentration of 4 wt %, FIG. 4B stearic acid amide/hexadecanamide at a concentration of 4 wt %, FIG. 4C hexadecanamide/n-octanamide at a concentration of 4 wt %].

These results indicate that the mixture of stearic acid amide/n-octanamide and the mixture of hexadecanamide/n-octanamide can form gels at a wide variety of mixing ratios as compared with the gels with mixtures of stearic acid amide/hexadecanamide. In addition, the mixtures of two components had a lower minimum gelation concentration (2.0 wt %) than the minimum gelation concentration (3.0 wt % or 6.0 wt %) of the toluene solution of a single alkylamide derivative. These results indicate that the toluene solutions of the mixture of two alkylamide derivatives are likely to form a gel in comparison with the solutions of a single alkylamide derivative.

TABLE 4

Gel forming ability of gels with mixture of
two alkylamide derivatives 1

| Concentration | Toluene gel Composition of stearic acid amide/ hexadecanamide (mass ratio) | | | | | | |
|---|---|---|---|---|---|---|---|
| | 10/1 | 4/1 | 2/1 | 1/1 | 1/2 | 1/4 | 1/10 |
| 2.0 wt % | ○(TG) | ○(TG) | X | X | X | X | X |
| 3.0 wt % | ○(TG) | ○(TG) | X | X | X | X | X |
| 4.0 wt % | ○(TG) | ○(TG) | X | X | X | X | X |

○: no substance ran off (gelated),
TG: translucent gel,
X: ran off

TABLE 5

Gel forming ability of gels with mixture of
two alkylamide derivatives 2

| Concentration | Toluene gel Composition of stearic acid amide/ n-octanamide (mass ratio) | | | | | | |
|---|---|---|---|---|---|---|---|
| | 10/1 | 4/1 | 2/1 | 1/1 | 1/2 | 1/4 | 1/10 |
| 2.0 wt % | ○(TG) | ○(TG) | ○(TG) | X(PG) | X | ○(CG) | ○(CG) |
| 3.0 wt % | ○(TG) | ○(TG) | ○(TG) | ○(TG) | ○(CG) | ○(CG) | ○(CG) |
| 4.0 wt % | ○(TG) | ○(TG) | ○(TG) | ○(TG) | ○(CG) | ○(CG) | ○(CG) |

○: no substance ran off (gelated),
TG: translucent gel,
CG: clear gel
X: ran off,
PG: partial gel

TABLE 6

Gel forming ability of gels with mixture of
two alkylamide derivatives 3

| Concentration | Toluene gel Composition of hexadecanamide/ n-octanamide (mass ratio) | | | | | | |
|---|---|---|---|---|---|---|---|
| | 10/1 | 4/1 | 2/1 | 1/1 | 1/2 | 1/4 | 1/10 |
| 2.0 wt % | X | X | X | X | ○(CG) | ○(CG) | ○(CG) |
| 3.0 wt % | X(PG) | X(PG) | X(PG) | ○(TG) | ○(CG) | ○(CG) | ○(CG) |
| 4.0 wt % | ○(TG) | ○(TG) | ○(TG) | ○(TG) | ○(CG) | ○(CG) | ○(CG) |

○: no substance ran off (gelated),
TG: translucent gel,
CG: clear gel
X: ran off,
PG: partial gel Example 2: Gelation Test of Mixture of Alkylamide Derivatives 2

Figure 5:
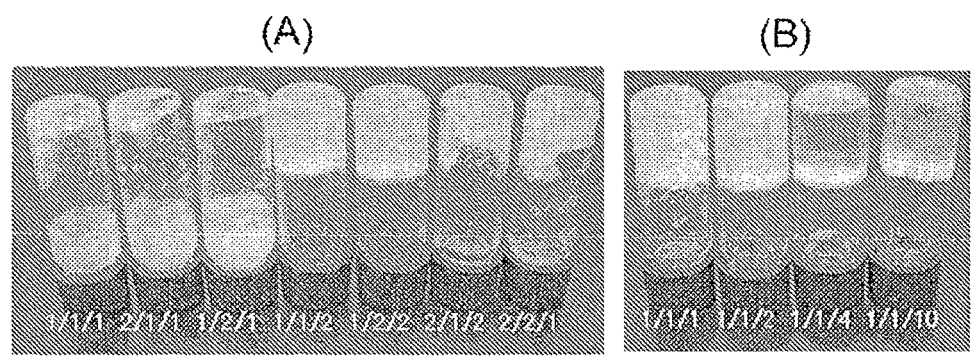
FIG. 5 includes photographs (4 wt % toluene gel) showing gelation behavior of toluene solutions of mixtures of three alkylamide derivatives at various mixing ratios in Example 2 and Example 3 (the numeric characters in the figures represent mixing ratios in terms of mass of stearic acid amide/hexadecanamide/n-octanamide).

Toluene solutions of a mixture of three alkylamide derivatives were subjected to the gelation test in the same procedure as in Comparative Examples 1 to 3. Toluene solutions of stearic acid amide/hexadecanamide/n-octanamide were prepared at various mixing ratios and concentrations (see Table 7, the concentration was a concentration of the mixture) and were subjected to the gelation test. Table 7 shows the observation results. Photographs of the sample tubes examined with the toluene solutions after cooling are shown in FIG. 5A [a concentration of 4 wt %].

These results indicate that the toluene solutions of the mixture of three alkylamide derivatives can also form a gel and the solution of a mixture containing n-octanamide at a high ratio is likely to form a gel even at a low concentration.

TABLE 7

Gel forming ability of gels with mixture of
three alkylamide derivatives 2

| Concentration | Toluene gel Composition of stearic acid amide/hexadecanamide/ n-octanamide (mass ratio) | | | | | | |
|---|---|---|---|---|---|---|---|
| | 1/1/1 | 2/1/1 | 1/2/1 | 1/1/2 | 1/2/2 | 2/1/2 | 2/2/1 |
| 3.0 wt % | X | X | X | X | X | X | X |
| 4.0 wt % | X(PG) | X(PG) | X(PG) | ○(CG) | ○(TG) | X(PG) | X(PG) |
| 5.0 wt % | ○(TG) | ○(TG) | ○(TG) | ○(TG) | ○(CG) | ○(CG) | ○(CG) |

○: no substance ran off (gelated),
TG: translucent gel,
CG: clear gel
X: ran off,
PG: partial gel Example 3: Gelation Test of Mixture of Alkylamide Derivatives 3

In the same procedure as in Comparative Example 1, the mixture containing n-octanamide at a high ratio and giving a good result in Example 2 among the toluene gels with a mixture of three alkylamide derivatives was studied by the gelation test of solutions containing n-octanamide at various ratios.

FIG. 5B shows the results obtained from toluene solutions of 4 wt % stearic acid amide/hexadecanamide/n-octanamide (the concentration was a concentration of the mixture) at various mixing ratios of 1/1/1, 1/1/2, 1/1/4, and 1/1/10.

These results indicate that a mixture containing n-octanamide having a short alkyl chain at a higher ratio forms a toluene gel having higher transparency.

Example 4: Gelation Test of Mixture of Alkylamide Derivatives 4

Fixed oils mixed with two alkylamide derivatives and fixed oils mixed with three alkylamide derivatives were subjected to the gelation test in the same procedure as in Comparative Examples 1 to 3. Fixed oil solutions of stearic acid amide/n-octanamide, stearic acid amide/hexadecanamide/n-octanamide, and erucic acid amide/behenic acid amide were prepared at various mixing ratios and concentrations (see Table 8, the concentration was a concentration of the mixture) and were subjected to the gelation test. Table 8 shows the observation results.

These results indicate that the fixed oil solution of the mixture of two alkylamide derivatives and of the mixture of three alkylamide derivatives can form a gel and the solution of a mixture containing n-octanamide at a high ratio is likely to form a gel even at a low concentration.

TABLE 8

Gel forming ability of gels with mixture of alkylamide derivatives 3

| | Composition of stearic acid amide/ n-octanamide (mass ratio) | | Composition of stearic acid amide/ hexadecanamide/ n-octanamide (mass ratio) | | Composition of erucic acid amide/ behenic acid amide (mass ratio) | | |
|---|---|---|---|---|---|---|---|
| Fixed oil | 1/1 | 1/10 | 1/1/1 | 1/1/10 | 10/1 | 1/1 | 1/10 |
| Olive oil | 2.0 (TG) | 1.0 (TG) | 2.0 (TG) | 1.0 (TG) | 1.0 (TG) | 1.0 (TG) | 2.0 (TG) |
| Squalane | 0.25 (CG) | 0.2 (CG) | 0.5 (CG) | 0.2 (CG) | 0.2 (TG) | 1.0 (TG) | 1.0 (TG) |

○: no substance ran off (gelated),
TG: translucent gel,
CG: clear gel
X: ran off,
PG: partial gel

Example 5: Transmittance Measurement of Gel with Mixture of Alkylamide Derivatives The toluene gels with a mixture of three alkylamide derivatives (4 wt %, the concentration was a concentration of the mixture) obtained in Example 3 and the toluene gels with a single alkylamide derivative (minimum gelation concentration) in Comparative Examples 1 to 3 were subjected to transmittance measurement at a wavelength from 400 nm to 700 nm.

Table 9 shows the obtained results. These spectroscopic results also indicate that a mixture containing n-octanamide having a short alkyl chain at a higher ratio forms a toluene gel having higher transparency.

TABLE 9

Transmittance of gels with mixture of three alkylamide derivatives

| | Transmittance (T %) | | | |
|---|---|---|---|---|
| Sample (mass ratio) | 400 nm | 500 nm | 600 nm | 700 nm |
| Gel with 3 wt % stearic acid amide | 0.15 | 0.00 | 0.02 | 0.01 |
| Gel with 6 wt % hexadecanamide | 0.12 | 0.03 | 0.00 | 0.02 |
| Gel with 3 wt % n-octanamide | 1.1 | 2.8 | 3.8 | 5.6 |
| Gel with 4 wt % mixture of three components at 1/1/2* | 0.18 | 0.15 | 0.24 | 0.34 |
| Gel with 4 wt % mixture of three components at 1/1/4* | 0.79 | 6.3 | 24.2 | 45.2 |
| Gel with 4 wt % mixture of three components at 1/1/10* | 1.2 | 11.6 | 29.9 | 48.9 |

*Mixing ratio of stearic acid amide/hexadecanamide/n-octanamide in terms of mass

Example 6: Thermal Behavior of Gel with Mixture of Alkylamide Derivatives

The toluene gels with a mixture of three alkylamide derivatives (4 wt %, the concentration was a concentration of the mixture) obtained in Example 3 and the toluene gels with a single alkylamide derivative (minimum gelation concentration for each derivative) in Comparative Examples 1 to 3 were prepared in accordance with the above procedures.

Figure 6:
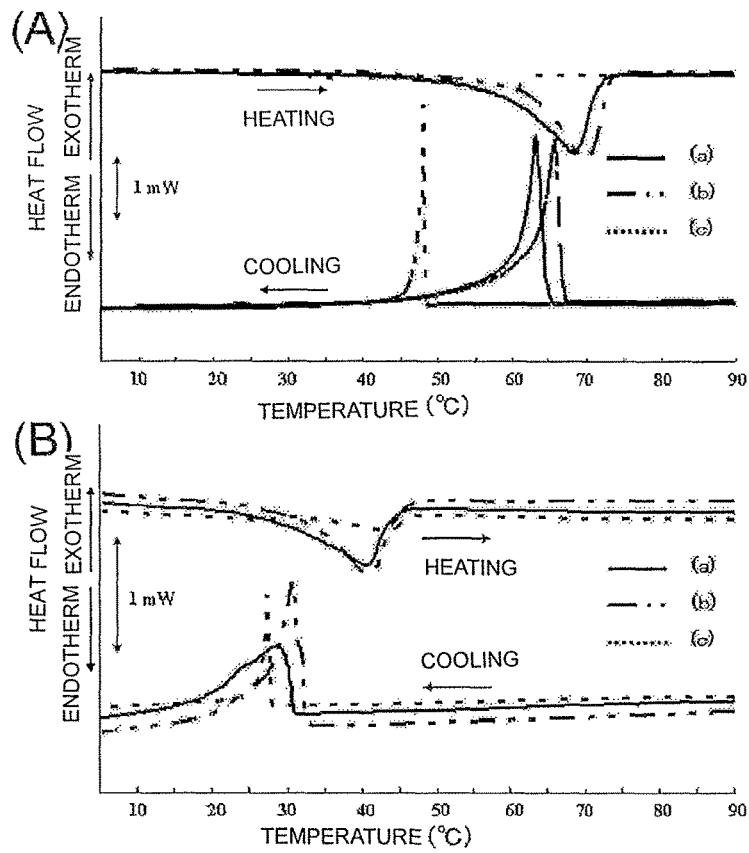
FIG. 6 includes views showing differential scanning calorimetry results of gels with a single alkylamide derivative and toluene gels with a mixture of three alkylamide derivatives at various mixing ratios in Example 6

The sol-gel transition temperature and the gel-sol transition temperature of each gel were determined with a differential scanning calorimeter. The obtained results are listed in Table 10 and FIG. 6 [FIG. 6A: (a) a toluene gel with 3 wt % stearic acid amide, (b) a toluene gel with 6 wt % hexadecanamide, (c) a toluene gel with 3 wt % n-octanamide; FIG. 6B: (a) a toluene gel with 4 wt % stearic acid amide/hexadecanamide/n-octanamide at a mixing ratio of 1/1/2 in terms of mass, (b) a toluene gel with 4 wt % stearic acid amide/hexadecanamide/n-octanamide at a mixing ratio of 1/1/4 in terms of mass, (c) a toluene gel with 4 wt % stearic acid amide/hexadecanamide/n-octanamide at a mixing ratio of 1/1/10 in terms of mass].

TABLE 10

Thermal behavior of gels with mixture of three alkylamide derivatives

| Sample (mass ratio) | $T_{gel\ to\ sol}/°$ C. ($\Delta H/mJ\ mg^{-1}$) | $T_{sol\ to\ gel}/°$ C. ($\Delta H/mJ\ mg^{-1}$) |
|---|---|---|
| Gel with 3 wt % stearic acid amide | 56 (30.7) | 67 (30.5) |
| Gel with 6 wt % hexadecanamide | 61 (53.2) | 68 (51.9) |
| Gel with 3 wt % n-octanamide | 46 (13.9) | 49 (13.7) |
| Gel with 4 wt % mixture of three components at 1/1/2* | 25 (12.1) | 31 (12.0) |
| Gel with 4 wt % mixture of three components at 1/1/4* | 27 (13.7) | 34 (14.5) |
| Gel with 4 wt % mixture of three components at 1/1/10* | 14, 43** (5.1) | 28 (4.6) |

*Mixing ratio of stearic acid amide/hexadecanamide/n-octanamide in terms of mass
**Bimodal peaks (peak temperature)

As listed in Table 10, it was ascertained that the gels with a single alkylamide derivative as the gelator and the gels with a mixture of three components undergo sol-gel transition quantitatively.

Figure 7:
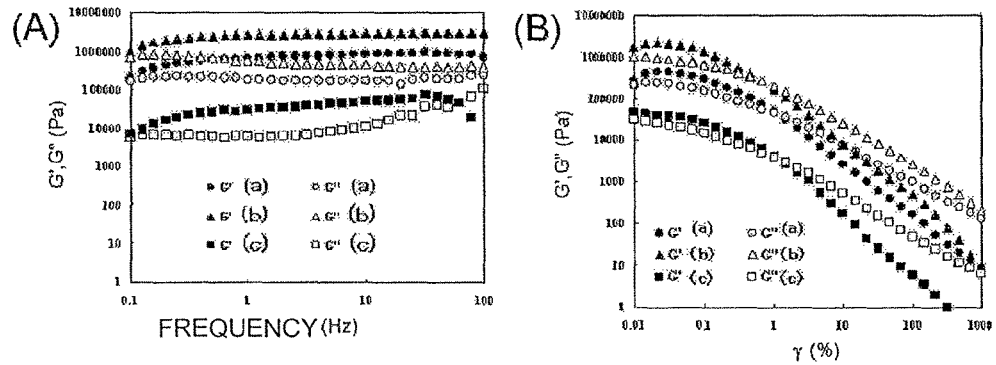
FIG. 7 includes views showing evaluation results of viscoelastic characteristics of gels with a single alkylamide derivative in Example 7

Example 7: Viscoelastic Characteristic Evaluation of Gel with Single Alkylamide Derivative and Gel with Mixture of Three Components Toluene gels with a mixture of three alkylamide derivatives (4 wt %, the concentration was a concentration of the mixture) and toluene gels with a single alkylamide derivative (minimum gelation concentration for each derivative) were prepared in accordance with the above procedures. The viscoelastic evaluations of the gels were carried out to examine gel states from the viewpoint of mechanical properties. The obtained results are shown in FIG. 7 (gels with a single component: (a) a toluene gel with 3 wt % stearic acid amide, (b) a toluene gel with 6 wt % hexadecanamide, (c) a toluene gel with 3 wt % n-octanamide) and FIG. 8 (gels with a mixture of three components: (a) a toluene gel with 4 wt % stearic acid amide/hexadecanamide/n-octanamide at a mixing ratio of 1/1/2 in terms of mass, (b) a toluene gel with 4 wt % stearic acid amide/hexadecanamide/n-octanamide at a mixing ratio of 1/1/4 in terms of mass, (c) a toluene gel with 4 wt % stearic acid amide/hexadecanamide/n-octanamide at a mixing ratio of 1/1/10 in terms of mass).

As shown in FIG. 7A and FIG. 8A (frequency dependence measurement), both the gels with a single component and the gels with a mixture of three components showed substantially plateau storage elastic moduli (G') and loss moduli (G") independent of the frequencies and also show G'>G", and thus it was ascertained that the samples measured were in a gel state (solid state).

As shown in FIG. 7B and FIG. 8B (strain dependence measurement), the samples showed substantially plateau storage elastic moduli G' and loss moduli G" at the initial strain, but the relation was reversed into G'<G" by an increase in the strain (around 0.1 to 1.0%), and thus it was ascertained that the samples were converted from a gel state (G'>G") to a liquid state (G'<G"). This mechanical examination revealed that the application of strain on a sample in a gel state causes gel-sol transition.

Example 8: Thixotropic Property Test of Gel with Single Alkylamide Derivative and Gel with Mixture of Two Components The behavior (thixotropic properties) of gels with a single alkylamide derivative and gels with a mixture (mixture of two components) were evaluated after gel pulverization.

<Thixotropic Property Test of Gel with Single Alkylamide Derivative>

In the same procedure as in Comparative Example 1 to Comparative Example 3, gels were prepared by using alkylamide derivatives (stearic acid amide, hexadecanamide, and n-octanamide) as the gelator and propylene carbonate, dichloroethane, toluene, SH245, and n-octane as the organic solvent at the minimum gelation concentrations listed in Table 1 and at concentrations 1 wt % higher than the minimum gelation concentrations.

The sample tube was next applied to a vortex mixer to pulverize the gel in the sample tube for 2 seconds, and was allowed to stand for a predetermined period of time (1 minute, 10 minutes, 1 hour, or 12 hours). The sample tube was placed in reverse, and whether the gel flowed was observed.

FIG. 9 shows the thixotropic behavior of the gels formed from toluene with various alkylamide derivatives at minimum gelation concentrations. FIG. 9 shows the toluene gels before pulverization as (a) to (c) [(a) a gel with 3 wt % stearic acid amide, (b) a gel with 6 wt % hexadecanamide, (c) a gel with 3 wt % n-octanamide] and the behavior of the gels that were pulverized for 2 seconds, then allowed to stand for 12 hours, and placed in reverse as (d) to (f) [(d) a gel with 3 wt % stearic acid amide after pulverization, (e) a gel with 6 wt % hexadecanamide, (f) a gel with 3 wt % n-octanamide].

Each gel sample formed from any organic solvent with any alkylamide derivative at a minimum gelation concentration or at a concentration 1 wt % higher than the minimum gelation concentration ran off at any predetermined period of time after the gel was pulverized and allowed to stand. The various gels with a single alkylamide derivative in the present test example exhibited no thixotropic properties.

<Thixotropic Property Test of Gels with Mixture of Alkylamide Derivatives (Mixture of Two Components)>

The behavior of gels with a mixture of alkylamide derivatives (mixture of two components) was evaluated after gel pulverization at various mixing ratios (see Table 11 to Table 13).

In the same procedure as in Example 1, toluene gels were prepared by using mixtures of stearic acid amide/hexadecanamide, mixtures of stearic acid amide/n-octanamide, and mixtures of hexadecanamide/n-octanamide at various mixing ratios (see Table 11 to Table 13) at concentrations of 2 to 4 wt % (the concentration was a concentration of the mixture) (at this point, compositions forming no gel are indicated by oblique lines in Table 11 to Table 13). The sample tube was next applied to a vortex mixer, and the gel in the sample tube was pulverized for 2 seconds by mechanical vibration into a sol state and was allowed to stand for a predetermined period of time (1 minutes, 10 minutes, 1 hour, or 12 hours). The sample tube was placed in reverse, and whether the gel flowed was observed. For samples that were once turned into a sol state and then returned into a gel state, minimum standing times (the time required for returning into a gel state after pulverization) are listed in Table 11 (gels with mixtures of stearic acid amide/hexadecanamide), Table 12 (gels with mixtures of stearic acid amide/n-octanamide), and Table 13 (gels with mixtures of hexadecanamide/n-octanamide).

TABLE 11

Thixotropic properties of gels with mixture of two components after pulverization 1

| Concentration | Composition of toluene gel with stearic acid amide/ hexadecanamide (mass ratio) | | | | | | |
|---|---|---|---|---|---|---|---|
| (as mixture) | 10/1 | 4/1 | 2/1 | 1/1 | 1/2 | 1/4 | 1/10 |
| 2.0 wt % | X* | X* | / | / | / | / | / |
| 3.0 wt % | X* | X* | / | / | / | / | / |
| 4.0 wt % | X* | X* | / | / | / | / | / |

X: ran off even after 12 h
*Separated into two phases of gel and solvent
Oblique line: form no gel from the outset

TABLE 12

Thixotropic properties of gels with mixture of two components after pulverization 2

| Concentration | Composition of toluene gel with stearic acid amide/ n-octanamide (mass ratio) | | | | | | |
|---|---|---|---|---|---|---|---|
| (as mixture) | 10/1 | 4/1 | 2/1 | 1/1 | 1/2 | 1/4 | 1/10 |
| 2.0 wt % | X | X | 12 h | / | / | 10 min | 1 h |
| 3.0 wt % | X | X | 10 min | 10 min | 10 min | 10 min | 1 h |
| 4.0 wt % | X | 1 h | 10 min | 10 min | 10 min | 10 min | 1 h |

X: ran off even after 12 h
Oblique line: form no gel from the outset

TABLE 13

Thixotropic properties of gels with mixture of two components after pulverization 3

| Concentration | Composition of toluene gel with hexadecanamide/ n-octanamide (mass ratio) | | | | | | |
|---|---|---|---|---|---|---|---|
| (as mixture) | 10/1 | 4/1 | 2/1 | 1/1 | 1/2 | 1/4 | 1/10 |
| 2.0 wt % | / | / | / | / | 12 h | 1 h | X |
| 3.0 wt % | / | / | / | 1 h | 1 h | 10 min | 12 h |
| 4.0 wt % | X* | X* | 1 h | 1 h | 1 h | 10 min | 12 h |

X: ran off even after 12 h.
*Separated into two phases of gel and solvent
Oblique line: form no gel from the outset As listed in Tables 12 and 13, as for the toluene gels with alkylamide derivatives, it was ascertained that the toluene gels with a single derivative failed to exhibit thixotropic properties, but the toluene gels with a mixture of two components, for example, stearic acid amide/n-octanamide, exhibited thixotropic properties in some cases. As listed in Table 11, some combinations, for example, mixtures of stearic acid amide/hexadecanamide, not only failed to form gels exhibiting thixotropic properties but also formed no gel. The results revealed that appropriate selection of mixtures and mixing ratios is essential for the expression of thixotropic properties and the formation of gels.

The studies on gels with a mixture are described, for example, by K. Hanabusa et al., J. Chem. Soc., Chem. Commun., (1993), pp. 1382-1384 and are reviewed by D. K. Smith et al., Chem. Eur. J., (2005), vol. 11, pp. 5496-5508, C. A. Dreiss, Soft Matter., (2007), vol. 3, pp. 956-970, S. J.

Rowan et al., Chem. Soc. Rev., (2012), vol. 41, pp. 6089-6102, and other reviews. However, there is no report about such a novel effect (thixotropic properties) achieved by mixing two or more alkylamide derivatives having different alkyl chain lengths as in the present invention. As described above, the present examples show the results indicating specific effects of the gelator of the present invention.

Example 9: Thixotropic Property Test of Gel with Mixture of Three Alkylamide Derivatives The behavior of gels with a mixture of alkylamide derivatives (mixture of three components) was evaluated after gel pulverization at various mixing ratios.

In the same procedure as in Example 2 and Example 3, as the gels with a mixture of three components exhibiting an improvement in transparency, toluene gels were prepared by using mixtures of stearic acid amide/hexadecanamide/n-octanamide at various mixing ratios (see Tables 14 and 15) at concentrations of 3 to 5 wt % (the concentration was a concentration of the mixture) (at this point, compositions forming no gel are indicated by oblique lines in Tables 14 and 15). In addition, at the mixing ratio [stearic acid amide/hexadecanamide/n-octanamide at a mass ratio of 1/1/10] of the toluene gel having high transparency in Example 3, a propylene carbonate gel with 4 wt % mixture, a dichloroethane gel with 4 wt % mixture, an SH245 (a cyclic silicone manufactured by Dow Corning Toray Silicone Co., Ltd.) gel with 4 wt % mixture, and an n-octane gel with 4 wt % mixture were prepared (the concentration was a concentration of the mixture).

The sample tube was next applied to a vortex mixer, and the gel in the sample tube was pulverized for 2 seconds by mechanical vibration into a sol state and was allowed to stand for a predetermined period of time (1 minute, 5 minutes, 10 minutes, 1 hour, 2 hours, or 12 hours). The sample tube was placed in reverse, and whether the gel flowed was observed. Tables 14 and 15 list minimum standing times (the time required for returning into a gel state after pulverization) of the toluene gels that were once turned into a sol state and then returned into a gel state. Table 16 shows the behavior of the gels prepared from organic solvents other than toluene, after gel pulverization.

Figure 15:
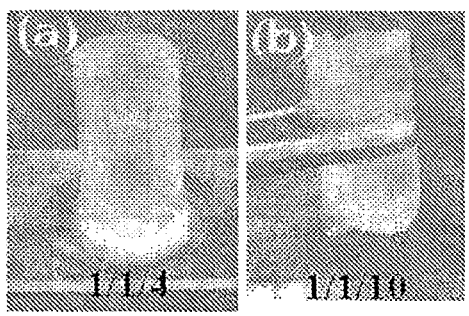
FIG. 15 includes photographs showing high mechanical strength of toluene gels with 4 wt % mixture of three alkylamide derivatives in Example 9 ((a) a toluene gel with stearic acid amide/hexadecanamide/n-octanamide at a mixing ratio of 1/1/4 in terms of mass that has been released from a sample tube and is capable of self-standing; (b) a toluene gel with stearic acid amide/hexadecanamide/n-octanamide at a mixing ratio of 1/1/10 in terms of mass that can be picked up with tweezers).

As an example, FIG. 10 shows the thixotropic property test results of the toluene gels with 4 wt % mixtures of three components (stearic acid amide/hexadecanamide/n-octanamide at mass ratios of 1/1/2, 1/1/4, and 1/1/10). FIG. 10 shows the behavior of the toluene gels that were pulverized for 2 seconds, then allowed to stand for 1 minute and 5 minutes, and placed in reverse. FIG. 15 shows the toluene gels with 4 wt % mixtures of three components (stearic acid amide/hexadecanamide/n-octanamide at mass ratios of 1/1/4 and 1/1/10) released from the sample tube.

TABLE 14

Thixotropic properties of toluene gels with mixture of three alkylamide derivatives after pulverization 1

| Concentration | Composition of toluene gel with stearic acid amide/hexadecanamide/n-octanamide (mass ratio) | | | | | | |
|---|---|---|---|---|---|---|---|
| (as mixture) | 1/1/1 | 2/1/1 | 1/2/1 | 1/1/2 | 1/2/2 | 2/1/2 | 2/2/1 |
| 3.0 wt % | / | / | / | / | / | / | / |
| 4.0 wt % | / | / | / | 1 h | 12 h | / | / |
| 5.0 wt % | 1 h | 1 h | 1 h | 10 min | 2 h | 1 h | 1 h |

Oblique line: form no gel from the outset

TABLE 15

Thixotropic properties of toluene gels with mixture of three alkylamide derivatives after pulverization 2

| Concentration | Composition of toluene gel with stearic acid amide/hexadecanamide/n-octanamide (mass ratio) | | | |
|---|---|---|---|---|
| (as mixture) | 1/1/1 | 1/1/2 | 1/1/4 | 1/1/10 |
| 4.0 wt % | / | 5 min | 5 min | 1 min |
| 5.0 wt % | 1 h | 5 min | 5 min | 1 min |

Oblique line: form no gel from the outset

TABLE 16

Thixotropic properties of gel of various solvents with mixture of three alkylamide derivatives after pulverization 3

| Time after pulverization | Various solvents with 4 wt % stearic acid amide/hexadecanamide/n-octanamide at 1/1/10 (mass ratio) | | | |
|---|---|---|---|---|
| | Propylene carbonate | Dichloroethane | SH245 | n-Octane |
| After 1 minute | X | X | X | X |
| After 10 minutes | X | X | X | Δ |
| After 1 hour | X | X | Δ | Δ |
| After 12 hours | X | ○ | ○ | ○ |

○: no substance ran off,
Δ: partially ran off,
X: ran off

<Thixotropic Property Test of Gels of Fixed Oils with Single Alkylamide Derivative>

In the same procedure as in Comparative Example 6 to Comparative Example 8, Comparative Example 11, and Comparative Example 12, gels were prepared by using alkylamide derivatives (stearic acid amide, hexadecanamide, n-octanamide, erucic acid amide, and behenic acid amide) as the gelator and olive oil and squalane as the fixed oil at the minimum gelation concentrations listed in Table 3 and at a concentrations 1 wt % higher than the minimum gelation concentrations.

The sample tube was next applied to a vortex mixer, and the gel in the sample tube was pulverized for 2 seconds and was allowed to stand for a predetermined period of time (1 minute, 10 minutes, 1 hour, or 12 hours). The sample tube was placed in reverse, and whether the gel flowed was observed.

FIGS. 11 and 12 show the thixotropic behavior of the gels formed from squalane with various alkylamide derivatives at minimum gelation concentrations. FIGS. 11 and 12 show the gels before pulverization as (a) to (c) and (a) to (b) [in FIG. 11, (a) a gel with 2 wt % stearic acid amide, (b) a gel with 2 wt % hexadecanamide, (c) a gel with 1 wt % n-octanamide; in FIG. 12, (a) a gel with 2 wt % erucic acid amide, (b) a gel with 2 wt % behenic acid amide] and the behavior of the gels that were pulverized for 2 seconds, then allowed to stand for 12 hours, and placed in reverse as (d) to (f) and (d) to (e) [in FIG. 11, (d) a gel with 2 wt % stearic acid amide after pulverization, (e) a gel with 2 wt % hexadecanamide, (f) a gel with 2 wt % n-octanamide; in FIG. 12, (d) a gel with 2 wt % erucic acid amide, (e) a gel with 2 wt % behenic acid amide].

Each gel sample formed from any fixed oil with any alkylamide derivative at a minimum gelation concentration or at a concentration 1 wt % higher than the minimum gelation concentration ran off or caused separation of oil from the gel at any predetermined period of time after the gel was pulverized and allowed to stand. The various gels with a single alkylamide derivative in the present test example exhibited no thixotropic properties.

Example 10: Thixotropic Property Test of Gels of Fixed Oils with Mixture of Two Alkylamide Derivatives or with Mixture of Three Alkylamide Derivatives The behavior of gels of fixed oils with a mixture of alkylamide derivatives (a mixture of two components and a mixture of three components) was evaluated after gel pulverization at various mixing ratios.

In the same procedure as in Example 2 and Example 3, olive oil gels and squalane gels were prepared by using mixtures of stearic acid amide/n-octanamide and mixtures of stearic acid amide/hexadecanamide/n-octanamide at various mixing ratios (see Tables 17, 18, and 19) at concentrations of 0.2 to 1.0 wt % (the concentration was a concentration of the mixture) (at this point, compositions forming no gel are indicated by oblique lines in Tables 17 and 18). In addition, olive oil gels and squalane gels with 1.0 and 2.0 wt % mixtures of erucic acid amide/behenic acid amide (the concentration was a concentration of the mixture) were prepared.

The sample tube was next applied to a vortex mixer, and the gel in the sample tube was pulverized for 2 seconds by mechanical vibration into a sol state and was allowed to stand for a predetermined period of time (1 minute, 3 minutes, 5 minutes, 10 minutes, 30 minutes, 1 hour, 2 hours, or 12 hours). The sample tube was placed in reverse, and whether the gel flowed was observed. Tables 17, 18, and 19 list minimum standing times (the time required for returning into a gel state after pulverization) of the toluene gels that were once turned into a sol state and then returned into a gel state.

As an example, FIG. 13 shows the thixotropic property test result of the squalane gel with 1 wt % mixture of three components (stearic acid amide/hexadecanamide/n-octanamide at a mass ratio of 1/1/10), and FIG. 14 shows the thixotropic property test result of the squalane gel with a mixture of two components (erucic acid amide/behenic acid amide at a mass ratio of 1/1).

TABLE 17

Thixotropic properties of olive oil gels with mixture of alkylamide derivatives after pulverization

| Concentration | Composition of stearic acid amide/n-octanamide or stearic acid amide/hexadecanamide/n-octanamide (mass ratio) | | | |
|---|---|---|---|---|
| (as mixture) | 1/1 | 1/10 | 1/1/1 | 1/1/10 |
| 1.0 wt % | / | 30 min | / | 5 min |
| 2.0 wt % | 10 min | 10 min | X | 3 min |

Oblique line: form no gel from the outset,
X: ran off even after 12 h

TABLE 18

Thixotropic properties of squalane gels with mixture of alkylamide derivatives after pulverization

| Concentration | Composition of stearic acid amide/n-octanamide or stearic acid amide/hexadecanamide/n-octanamide (mass ratio) | | | |
|---|---|---|---|---|
| (as mixture) | 1/1 | 1/10 | 1/1/1 | 1/1/10 |
| 0.5 wt % | X | X | X | X |
| 1.0 wt % | X | 10 min | X | 10 min |
| 2.0 wt % | 12 h | 1 min | X | 5 min |

Oblique line: form no gel from the outset,
X: ran off even after 12 h

TABLE 19

Thixotropic properties of olive oil gels with mixture of alkylamide derivatives after pulverization 2

| Concentration | Composition of erucic acid amide/behenic acid amide (mass ratio) | | |
|---|---|---|---|
| (as mixture) | 10/1 | 1/1 | 1/10 |
| 0.5 wt % | / | / | / |
| 1.0 wt % | 30 min | 30 min | X |
| 2.0 wt % | 1 min | 1 min | X |

Oblique line: form no gel from the outset,
X: ran off even after 12 h

TABLE 20

Thixotropic properties of squalane gels with mixture of alkylamide derivatives after pulverization 2

| Concentration | Composition of erucic acid amide/behenic acid amide (mass ratio) | | |
|---|---|---|---|
| (as mixture) | 10/1 | 1/1 | 1/10 |
| 0.5 wt % | X | X | / |
| 1.0 wt % | 30 min | 30 min | X |
| 2.0 wt % | 1 min | 1 min | X |

Oblique line: form no gel from the outset,
X: ran off even after 12 h

As listed in Tables 12, 13, 14, 15, 16, 18, 19, and 20, it was ascertained that the gels of organic solvents or fixed oils with alkylamide derivatives exhibit thixotropic properties when the alkylamide derivatives are a mixture of two components or a mixture of three components, such as a mixture of stearic acid amide/hexadecanamide/n-octanamide. In particular, as listed in Table 15 and FIG. 10, a gel formed with a mixture containing n-octanamide at a higher ratio than those of other two alkylamide derivatives is likely to exhibit thixotropic properties.

As listed in Table 16, it was ascertained that the gels of dichloroethane, SH245, and n-octane with a mixture of three alkylamide derivatives also exhibit thixotropic properties.

In addition, as listed in Tables 17 and 18, it was ascertained that the gels of fixed oils such as olive oil and squalane with a mixture of two alkylamide derivatives or a mixture of three alkylamide derivatives also exhibit thixotropic properties.

As listed in Tables 19 and 20, it was ascertained that the gels with a mixture of two components such as a mixture of erucic acid amide/behenic acid amide exhibit similar thixotropic properties.

As shown in FIG. 15, the gel with a mixture of three components at a selected optimum mixing ratio of three components had such a high mechanical strength that the gel was able to be released from a sample tube, was capable of self-standing (FIG. 15A), and was able to be picked up with tweezers (FIG. 15B).

As indicated above, it was ascertained that the toluene gel, the dichloroethane gel, the SH245 gel, the n-octane gel, the olive oil gel, and the squalane gel with a mixture of two alkylamide derivatives or a mixture of three alkylamide derivatives exhibit thixotropic properties.

As described above, there is no report about such a novel effect (thixotropic properties) achieved by mixing two or more alkylamide derivatives having different alkyl chain lengths as in the present invention. The results indicate specific effects of the gelator of the present invention.

Example 11: Gelation Test of Mixture of Alkylurea Derivatives 1

Figure 16:
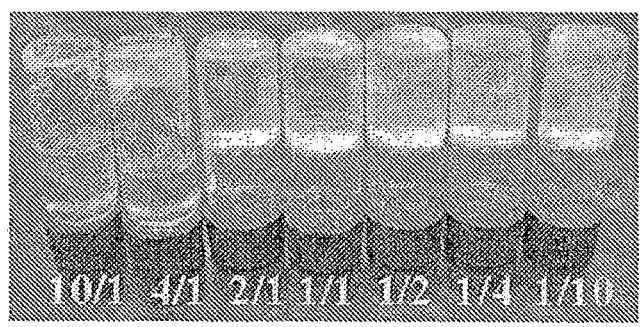
FIG. 16 is a photograph showing gelation behavior of toluene solutions of 3 wt % mixture of two alkylurea derivatives at various mixing ratios in Example 11 (octadecylurea/butylurea, the numeric characters in the figures represent mixing ratios in terms of mass).

Toluene solutions of a mixture of two alkylurea derivatives were subjected to the gelation test in the same procedure as in Comparative Example 1. Toluene solutions of octadecylurea and butylurea were prepared at various mixing ratios and concentrations (see Table 21, the concentration was a concentration of the mixture) and were subjected to the gelation test. Table 21 shows the observation results. Photographs of the sample tubes examined with the toluene solutions after cooling are shown in FIG. 16 [a concentration of 4 wt %].

These results indicate that the mixture of two components of octadecylurea and butylurea forms gels at a wide variety of mixing ratios and a mixture containing butylurea at a high ratio is likely to form a gel. In addition, the mixture of two alkylurea derivatives gave a lower minimum gelation concentration (1.0 wt %) than the minimum gelation concentration (2.0 wt % or 6.0 wt %) of the toluene solution of a single alkylurea derivative. These results indicate that the toluene solutions of the mixture of two alkylurea derivatives are likely to form a gel in comparison with the solutions of a single alkylurea derivative.

TABLE 21

Gel forming ability of gels with mixture of two alkylurea derivatives 1

| Concentration | Composition of toluene gel with octadecylurea/butylurea (mass ratio) | | | | | | |
|---|---|---|---|---|---|---|---|
| | 10/1 | 4/1 | 1/2 | 1/1 | 1/2 | 1/4 | 1/10 |
| 0.5 wt % | X | X | X | X | X | X | X |
| 1.0 wt % | X | X | X | X | X | ○(CG) | ○(CG) |
| 2.0 wt % | X | X | X | ○(CG) | ○(CG) | ○(CG) | ○(CG) |
| 3.0 wt % | X | X(PG) | ○(CG) | ○(CG) | ○(CG) | ○(CG) | ○(CG) |
| 4.0 wt % | X | X(PG) | ○(CG) | ○(CG) | ○(CG) | ○(CG) | ○(CG) |

○: no substance ran off (gelated),
CG: clear gel
X: ran off,
PG: partial gel

Example 12: Gelation Test of Mixture of Alkylurea Derivatives 2

Fixed oils mixed with two alkylurea derivatives were subjected to the gelation test in the same procedure as in Comparative Example 1. Fixed oil solutions of octadecylurea/butylurea were prepared at various mixing ratios and concentrations (see Table 22, the concentration was a concentration of the mixture) and were subjected to the gelation test (only isopropyl myristate that formed a gel with a single component was subjected to the test). Table 22 shows the observation results.

These results indicate that the isopropyl myristate solutions of a mixture of two alkylurea derivatives also form a gel.

TABLE 22

Gel forming ability of gels with mixture of alkylurea derivatives 2

| | Composition of octadecylurea/butylurea (mass ratio) | |
|---|---|---|
| | 1/1 | 1/10 |
| Fixed oil | | |
| Isopropyl myristate | 0.5 (TG) | 0.5 (TG) |

○: no substance ran off (gelated),
TG: translucent gel

Example 13: Transmittance Measurement of Gel with Mixture of Alkylurea Derivatives The toluene gels with a mixture of two alkylurea derivatives (3 wt %, the concentration was a concentration of the mixture) obtained in Example 11 and the toluene gels with a single alkylurea derivative (minimum gelation concentration) in Comparative Examples 4 and 5 were subjected to transmittance measurement at a wavelength from 400 nm to 700 nm.

Table 23 shows the obtained results. These spectroscopic results also indicate that a mixture containing butylurea having a short alkyl chain at a higher ratio forms a toluene gel having higher transparency.

TABLE 23

Transmittance of gels with mixture of two alkylurea derivatives

| Sample (mass ratio) | Transmittance (T %) | | | |
|---|---|---|---|---|
| | 400 nm | 500 nm | 600 nm | 700 nm |
| Gel with 2 wt % octadecylurea | 0.14 | 0.04 | 0.03 | 0.02 |
| Gel with 6 wt % butylurea | 0.07 | 0.03 | 0.04 | 0.07 |
| Gel with 3 wt % mixture of two components at 2/1* | 8.5 | 4.7 | 3.4 | 3.8 |
| Gel with 3 wt % mixture of two components at 1/1* | 9.4 | 7.6 | 6.5 | 7.9 |
| Gel with 3 wt % mixture of two components at 1/2* | 4.7 | 5.3 | 6.6 | 9.6 |
| Gel with 3 wt % mixture of two components at 1/4* | 4.5 | 3.7 | 5.9 | 10.2 |
| Gel with 3 wt % mixture of two components at 1/10* | 4.2 | 1.7 | 1.2 | 1.8 |

*Mixing ratio of octadecylurea/butylurea (mass ratio)

Example 14: Thermal Behavior of Gel with Mixture of Alkylurea Derivatives

The toluene gels with a mixture of two alkylurea derivatives (3 wt %, the concentration was a concentration of the mixture) obtained in Example 11 and the toluene gels with a single alkylurea derivative (minimum gelation concentration) in Comparative Examples 4 and 5 were prepared in accordance with the above procedures.

The sol-gel transition temperature and the gel-sol transition temperature of each gel were determined with a differential scanning calorimeter. The obtained results are listed in Table 24 and FIG. 17 [FIG. 17A: (a) a toluene gel with 2 wt % octadecylurea, (b) a toluene gel with 6 wt % butylurea; FIG. 17B: (a) a toluene gel with 3 wt % octadecylurea/butylurea at a mixing ratio of 1/1 in terms of mass, (b) a toluene gel with 3 wt % octadecylurea/butylurea at a mixing ratio of 1/2 in terms of mass, (c) a toluene gel with 3 wt % octadecylurea/butylurea at a mixing ratio of 1/4 in terms of mass, (d) a toluene gel with 3 wt % octadecylurea/butylurea at a mixing ratio of 1/10 in terms of mass].

TABLE 24

Thermal behavior of gels with mixture of two alkylurea derivatives

| Sample (mass ratio) | $T_{gel\ to\ sol}/°\ C.$ ($\Delta H/mJmg^{-1}$) | $T_{sol\ to\ gel}/°\ C.$ ($\Delta H/mJmg^{-1}$) |
|---|---|---|
| Gel with 3 wt % octadecylurea | 67 (8.1) | 65 (8.5) |
| Gel with 6 wt % butylurea | 64 (16.1) | 58 (16.1) |
| Gel with 3 wt % mixture of two components at 1/1* | 41 (4.7) | 39, 36** (4.8) |
| Gel with 3 wt % mixture of two components at 1/2* | 56**, 41 (4.2) | 46, 37** (4.1) |
| Gel with 3 wt % mixture of two components at 1/4* | 21, 42** (3.8) | 33, 29, 20 (3.7) |
| Gel with 3 wt % mixture of two components at 1/10* | 37, 60** (2.0) | 40, 31** (2.1) |

*Mixing ratio of octadecylurea/butylurea (mass ratio)
**Bimodal peaks (peak temperature).

As listed in Table 24, it was ascertained that the gels with a single alkylurea derivative as the gelator and the gels with a mixture of two components undergo sol-gel transition quantitatively.

Figure 18:
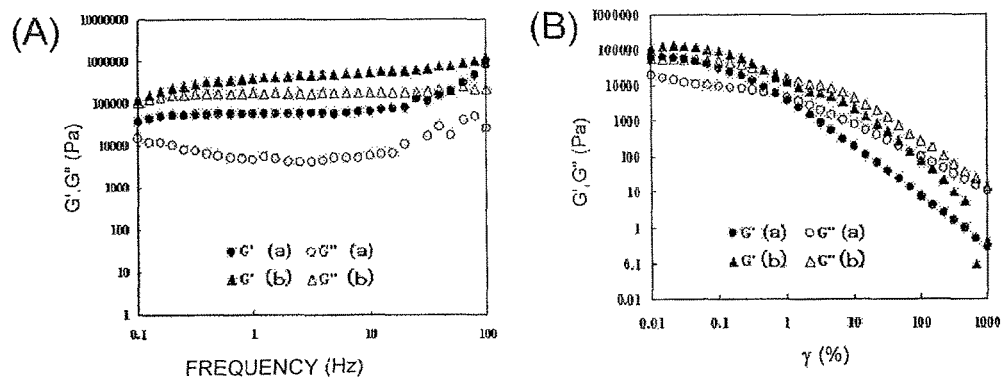
FIG. 18 includes views showing evaluation results of viscoelastic characteristics of gels with a single alkylurea derivative in Example 15
Figure 19:
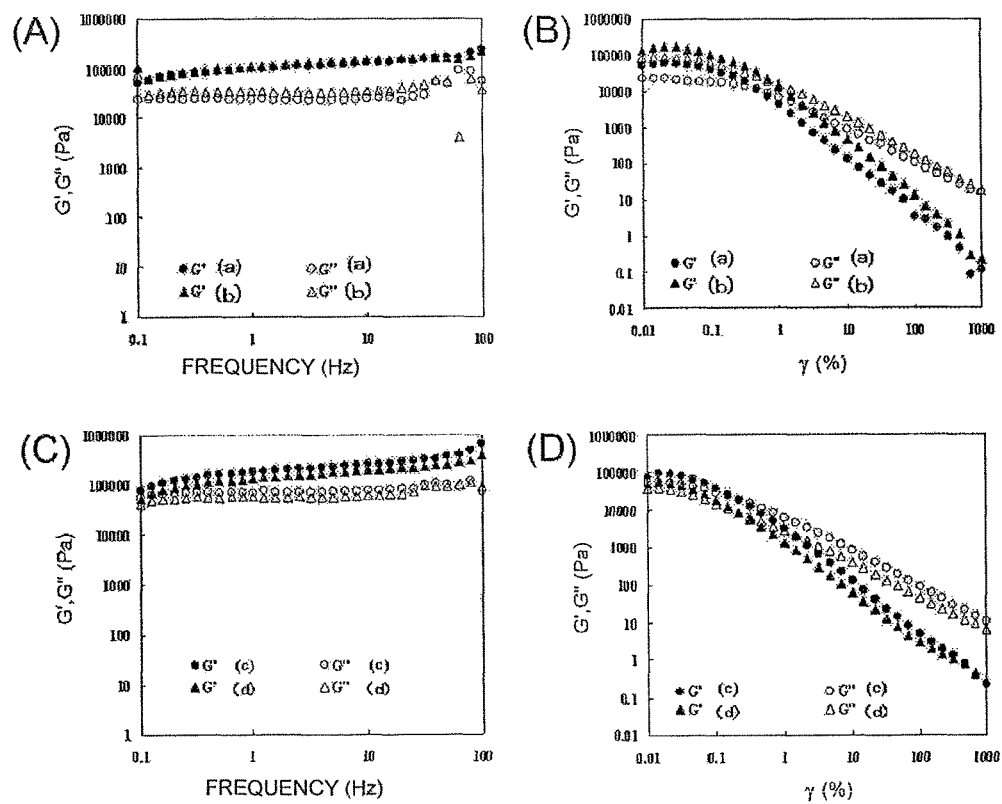
FIG. 19 includes views showing evaluation results of viscoelastic characteristics of gels with a mixture of two alkylureas in Example 15

Example 15: Viscoelastic Characteristic Evaluation of Gel with Single Alkylurea Derivative and Gel with Mixture The toluene gels with a mixture of two alkylurea derivatives (3 wt %, the concentration was a concentration of the mixture) and the toluene gels with a single alkylurea derivative (minimum gelation concentration) were prepared in accordance with the above procedures. The viscoelastic evaluations of the gels were carried out to examine gel states from the viewpoint of mechanical properties. The obtained results are shown in FIG. 18 (gels with a single component: (a) a toluene gel with 2 wt % octadecylurea, (b) a toluene gel with 6 wt % butylurea) and FIG. 19 (gels with a mixture of two components: (a) a toluene gel with 3 wt % octadecylurea/butylurea at a mixing ratio of 1/1 in terms of mass, (b) a toluene gel with 3 wt % octadecylurea/butylurea at a mixing ratio of 1/2 in terms of mass).

As shown in FIG. 18A and FIGS. 19A and 19C (frequency dependence measurement), the samples showed substantially plateau storage elastic moduli (G') and loss moduli (G") independent of the frequencies and also showed G'>G", and thus it was ascertained that the samples measured are in a gel state (solid state).

As shown in FIG. 18B and FIGS. 19B and 19D (strain dependence measurement), the samples showed substantially plateau storage elastic moduli G' and loss moduli G" at the initial strain, but the relation was reversed into G'<G" by an increase in the strain (around 0.1 to 1.0%), and thus it was ascertained that the samples were converted from a gel state (G'>G") to a liquid state (G'<G"). This mechanical examination revealed that the application of strain on a sample in a gel state causes gel-sol transition.

Example 16: Thixotropic Property Test of Gels with Single Alkylurea Derivative and Gel with Mixture of Two Components The behavior (thixotropic properties) of gels with a single alkylurea derivative and gels with a mixture (mixture of two components) was evaluated after gel pulverization.
<Gel with Single Alkylurea Derivative>
In the same procedure as in Comparative Examples 4, Comparative Example 5, Comparative Example 11, and Comparative Example 12, gels were prepared by using alkylurea derivatives (octadecylurea and butylurea) as the gelator and propylene carbonate, dichloroethane, toluene, and isopropyl myristate as the organic solvent at the minimum gelation concentrations listed in Table 2 and at concentrations 0.5 to 1 wt % wt % higher than the minimum gelation concentrations.

The sample tube was next applied to a vortex mixer, and the gel in the sample tube was pulverized for 2 seconds and was allowed to stand for a predetermined period of time (1 minute, 10 minutes, 1 hour, or 12 hours). The sample tube was placed in reverse, and whether the gel flowed was observed.

FIGS. 20 and 21 show the thixotropic behavior of the gels formed from toluene and isopropyl myristate with various alkylurea derivatives at minimum gelation concentrations. FIGS. 20 and 21 show the gels before pulverization as (a) to (b) [in FIG. 20, (a) a toluene gel with 3 wt % octadecylurea, (b) a toluene gel with 6 wt % butylurea; in FIG. 21, (a) an isopropyl myristate gel with 1 wt % octadecylurea, (b) an isopropyl myristate gel with 1 wt % butylurea] and the behavior of the gels that were pulverized for 2 seconds, then allowed to stand for 12 hours, and placed in reverse as (c) to (d) [in FIG. 20, (c) a toluene gel with 3 wt % octadecylurea, (d) a toluene gel with 6 wt % butylurea; in FIG. 21, (c) an isopropyl myristate gel with 1 wt % octadecylurea, (d) an isopropyl myristate gel with 1 wt % butylurea].

Each gel sample formed from any organic solvent with any alkylurea derivative at a minimum gelation concentration or at a concentration 0.5 to 1 wt % higher than the minimum gelation concentration ran off at any predetermined period of time after the gel was pulverized and allowed to stand. The various gels with a single alkylurea derivative in the present test example exhibited no thixotropic properties.
<Thixotropic Property Test of Gels with Mixture of Alkylurea Derivatives (Mixture of Two Components)>
The behavior of gels with a mixture of two alkylurea derivatives was evaluated after gel pulverization at various mixing ratios (see Table 25).

In the same procedure as in Example 11, toluene gels were prepared at various mixing ratios (see Table 25) at concentrations of 0.5 to 4 wt % (the concentration was a concentration of the mixture) (at this point, compositions forming no gel are indicated by oblique lines in Table 25). In addition, at the mixing ratios of 1/4 and 1/10 in terms of mass of octadecylurea/butylurea giving good results, a propylene carbonate gel with 5.0 wt % mixture (minimum gelation concentration of the gel with the mixture) and a dichloroethane gel with 3.0 wt % mixture were prepared (the concentration was a concentration of the mixture).

The sample tube was next applied to a vortex mixer, and the gel in the sample tube was pulverized for 2 seconds by mechanical vibration into a sol state and was allowed to stand for a predetermined period of time (1 minute, 10 minutes, 1 hour, or 12 hours). The sample tube was placed in reverse, and whether the gel flowed was observed. Table 25 shows the minimum standing times (the time required for returning into a gel state after pulverization) of gels that were once turned into a sol state and then returned into a gel state, and Table 26 lists the behavior of gels of propylene carbonate and dichloroethane after pulverization.

FIG. 22 shows the gelation behavior (FIG. 22A: reversed samples before pulverization) and the thixotropic behavior (FIG. 22B: reversed samples that was allowed to stand for 1 minute after pulverization, FIG. 22C: reversed samples that were allowed to stand for 30 minutes after pulverization) of the toluene solutions of 3 wt % various alkylurea derivatives (mixture of two components) (the numeric characters in the figures represent mixing ratios of octadecylurealbutylurea in terms of mass).

Figure 23:
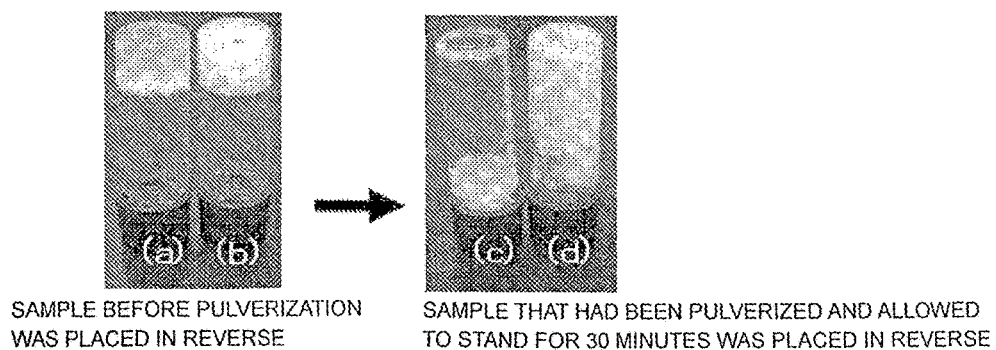
FIG. 23 includes photographs showing gelation behavior ((a), (b) reversed samples before pulverization: (a) 0.5 wt %, (b) 1.0 wt %) and thixotropic behavior ((c), (d) reversed sample that was allowed to stand for 30 minutes after pulverization: (c) 0.5 wt %, (d) 1.0 wt %) of isopropyl myristate solutions of two alkylurea derivatives (a mixture of octadecylurea/butylurea at a mixing ratio of 1/1 in terms of mass) in Example 16.

FIG. 23 shows the gelation behavior of the isopropyl myristate solutions of two alkylurea derivatives (a mixture of two components of octadecylurea/butylurea at a mixing ratio of 1/1 in terms of mass) ((a), (b) reversed samples before pulverization: (a) 0.5 wt %, (b) 1.0 wt %) and the thixotropic behavior ((c), (d) reversed samples that were allowed to stand for 30 minutes after pulverization: (c) 0.5 wt %, (d) 1.0 wt %).

TABLE 25

Thixotropic properties of toluene gels with mixture of two alkylurea derivatives 1

| Concen-tration | Composition of toluene gel with octadecylurea/butylurea | | | | | | |
|---|---|---|---|---|---|---|---|
| | 10/1 | 4/1 | 2/1 | 1/1 | 1/2 | 1/4 | 1/10 |
| 0.5 wt % | / | / | / | / | / | / | / |
| 1.0 wt % | / | / | / | / | / | X | X |
| 2.0 wt % | / | / | / | 12 h | 1 h | 12 h | 12 h |
| 3.0 wt % | / | / | X | 1 min | 1 min | 1 min | 1 h |
| 4.0 wt % | / | / | 12 h | 1 min | 1 min | 1 min | 1 min |

Oblique line: form no gel from the outset,

X: ran off even after 12 h

TABLE 26

Thixotropic properties of gels with mixture of two alkylurea derivatives after pulverization 2

| | Concentration and Composition (mass ratio) of toluene gel with octadecylurea/butylurea and solvent | | | |
|---|---|---|---|---|
| | 1/4 | | 1/10 | |
| Time after pulverization | Propylene carbonate (5.0 wt %) | Dichloro-ethane (3.0 wt %) | Propylene carbonate (5.0 wt %) | Dichloro-ethane (3.0 wt %) |
| After 1 minute | X | X | X | X |
| After 10 minutes | X | X | X | X |
| After 1 hour | X | X | X | X |
| After 12 hours | ○ | ○ | ○ | X |

○: no substance ran off,

X: ran off

TABLE 27

Thixotropic properties of gels of isopropyl myristate with mixture of two alkylurea derivatives after pulverization 3

| Concentration | Composition of octadecylurea/butylurea (mass ratio) | |
|---|---|---|
| (as mixture) | 1/1 | 1/10 |
| 0.5 wt % | X | X |
| 1.0 wt % | 30 min | X |

X: ran off even after 12 h

As listed in Table 25, as for the toluene gels with alkylurea derivatives, it was ascertained that the toluene gels with a single derivative failed to exhibit thixotropic properties, but the toluene gels with a mixture of two components, for example, octadecylurea/butylurea, exhibited thixotropic properties in some cases.

As listed in Table 26, it was ascertained that the gels of propylene carbonate and dichloroethane prepared with a mixture of two alkylurea derivatives also exhibit thixotropic properties.

As listed in Table 27, it was ascertained that the gels of isopropyl myristate as a fixed oil prepared with a mixture of two alkylurea derivatives also exhibit thixotropic properties.

As indicated above, it was ascertained that the propylene carbonate gel, the dichloroethane gel, the toluene gel, and the isopropyl myristate gel with a mixture of two alkylurea derivatives exhibit thixotropic properties.

As described above, there is no report about such a novel effect (thixotropic properties) achieved by mixing two or more alkylurea derivatives having different alkyl chain lengths as in the present invention. The results indicate specific effects of the gelator of the present invention.

Example 17: Thixotropic Property Test of Gel with Single Alkylamide Derivative and Gel with Mixture The behavior before and after gel pulverization of gels with a single alkylamide derivative and gels with a mixture (mixture of three components) were evaluated with a rheometer. The obtained results are shown in FIG. 24 [FIG. 24A: a toluene gel with 4 wt % mixture of three components of stearic acid amide/hexadecanamide/n-octanamide at a mass ratio of 1/1/10, FIG. 24B: a toluene gel with 3 wt % stearic acid amide alone, FIG. 24C: a toluene gel with 3 wt % hexadecanamide alone, FIG. 24D: a toluene gel with 3 wt % n-octanamide alone].

Figure 24:
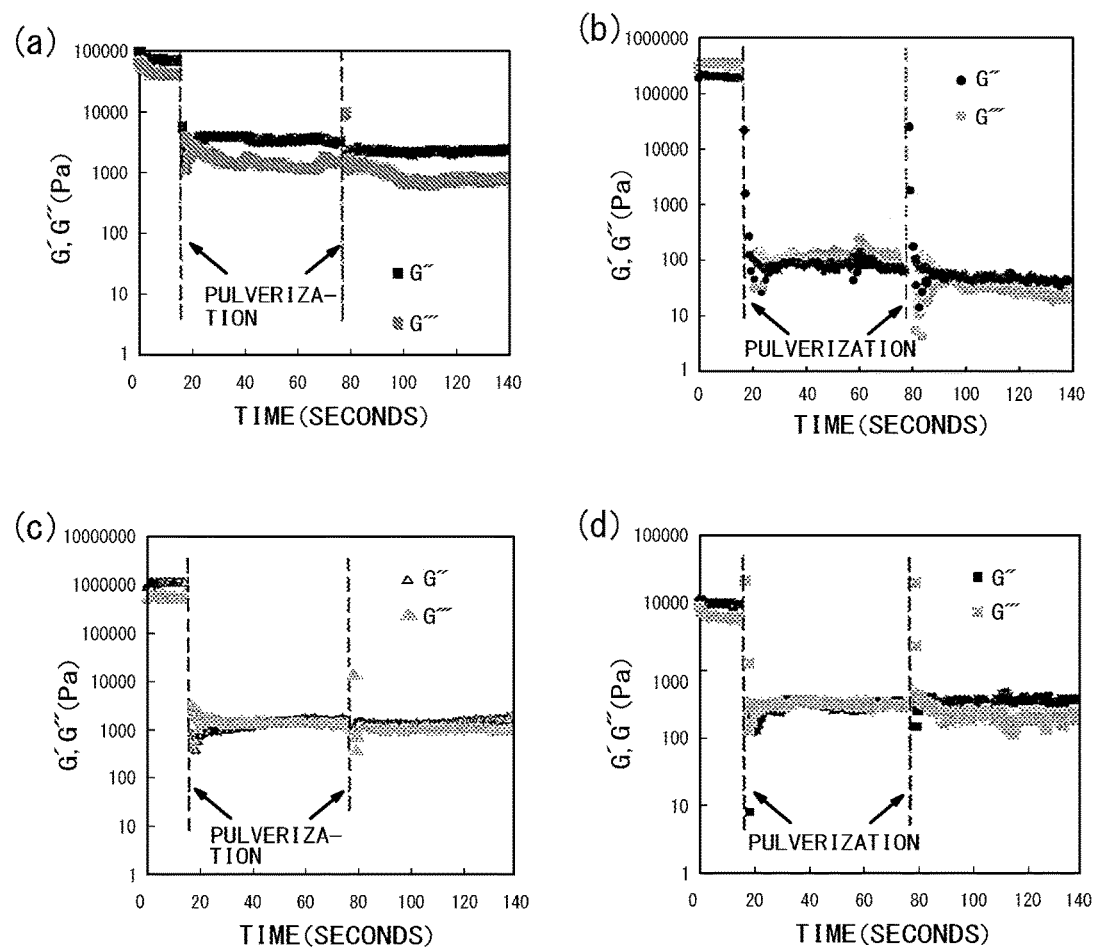
FIG. 24 includes views showing behavior evaluated with a rheometer before and after gel pulverization of gels with a single alkylamide derivative and a gel with a mixture (mixture of three components) in Example 17 (FIG. 24A: a toluene gel with 4 wt % stearic acid amide/hexadecanamide/n-octanamide at a mixing ratio of 1/1/10 in terms of mass, FIG. 24B: a toluene gel with 3 wt % stearic acid amide, FIG. 24C: a toluene gel with 3 wt % hexadecanamide, FIG. 24D: a toluene gel with 3 wt % n-octanamide).

As shown in FIG. 24, the gel with a mixture of three components (FIG. 24A) exhibited high recovery of the storage elastic modulus (G') and the loss modulus (G") after pulverization as compared with the gels with a single component (FIGS. 24B to 24D). Moreover, the gels with a single component exhibited G'>G" (a gel state to a liquid state) after recovery, whereas the gel with a mixture clearly exhibited G'>G" (a gel state) after recovery. This mechanical examination revealed that the gel with a mixture has higher thixotropic properties.

Example 18: Thixotropic Property Test of Gel with Single Alkylurea Derivative and Gel with Mixture The behavior before and after gel pulverization of gels with a single alkylurea derivative and gels with a mixture (mixture of two components) were evaluated with a rheometer. The obtained results are shown in FIGS. 25 [FIG. 25A: a toluene gel with 3 wt % mixture of two components of octadecylurea/butylurea at a mass ratio of 1/4, FIG. 25B: a toluene gel with 3 wt % mixture of two components of octadecylurea/butylurea at a mass ratio of 1/10, FIG. 25C: a toluene gel with 2 wt % octadecylurea alone, a toluene gel with 6 wt % butylurea alone].

Figure 25:
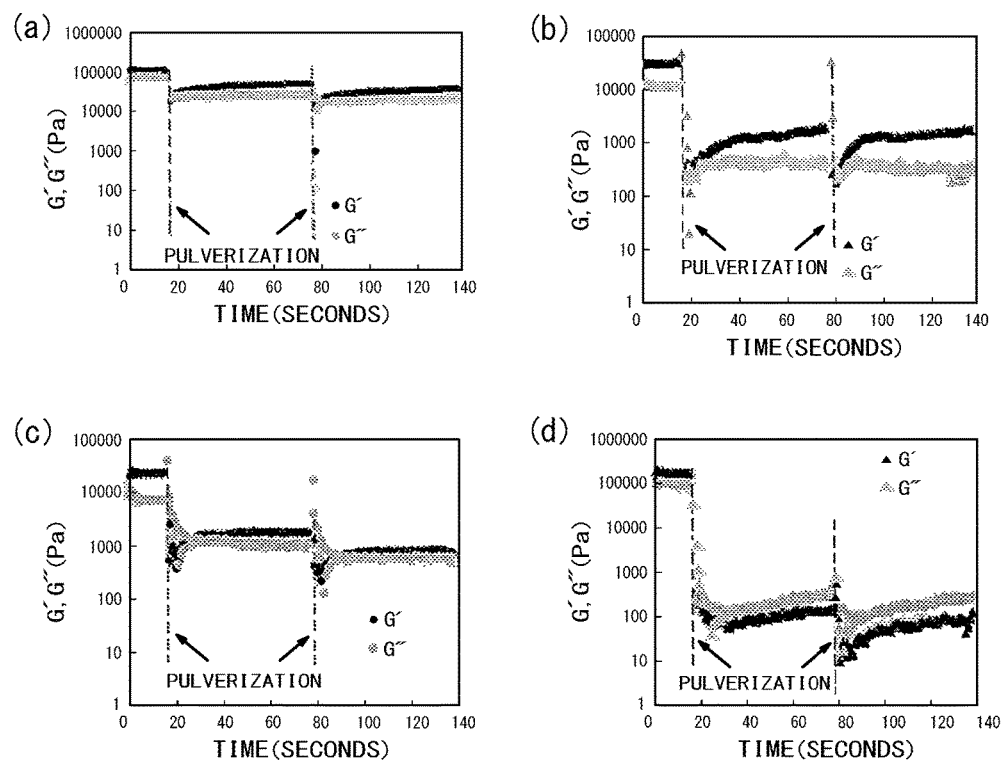
FIG. 25 includes views showing behavior evaluated with a rheometer before and after gel pulverization of gels with a single alkylurea derivative and gels with a mixture (mixture of two components) in Example 18 (FIG. 25A: a toluene gel with 3 wt % octadecylurea/butylurea at a mixing ratio of 1/4 in terms of mass, FIG. 25B: a toluene gel with 3 wt % octadecylurea/butylurea at a mixing ratio of 1/10 in terms of mass, FIG. 25C: a toluene gel with 2 wt % octadecylurea, FIG. 25D: a toluene gel with 6 wt % butylurea).

As shown in FIG. 25, the gels with a mixture of two components (FIGS. 25A and 25B) exhibited high recovery of the storage elastic modulus (G') and the loss modulus (G") as compared with the gels with a single component (FIGS. 25C and 25D). Moreover, the gels with a single component exhibited G'>G" (a gel state to a liquid state) after recovery, whereas the gels with a mixture clearly exhibited G'>G" (a gel state) after recovery. This mechanical examination revealed that the gel with a mixture has higher thixotropic properties.

Figure 26:
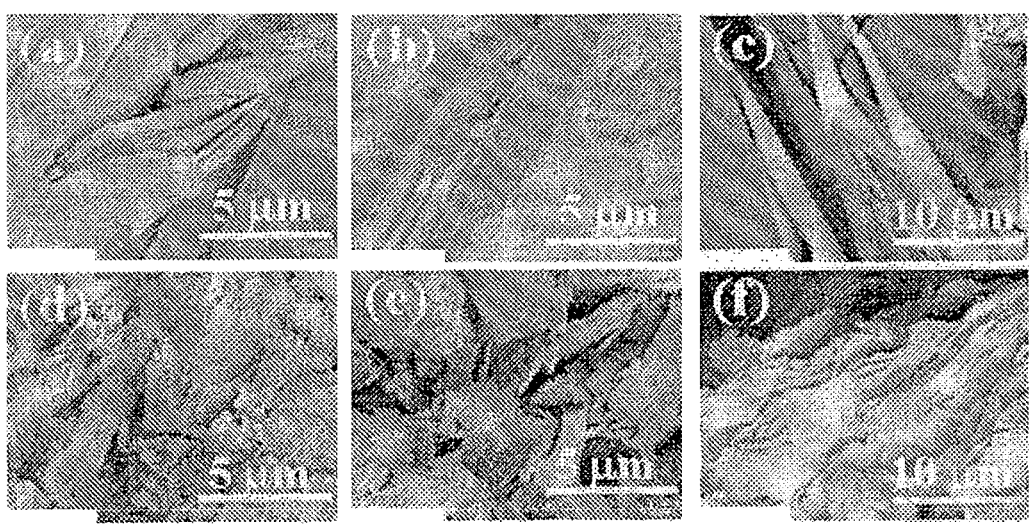
FIG. 26 includes scanning electron micrographs (SEM) of toluene xerogels with a single component of or with a mixture of various alkylamide derivatives (prepared from gels at minimum gelation concentrations) in Comparative Example 13 and Example 19 (FIG. 26A: a toluene xerogel with stearic acid amide, FIG. 26B: a toluene xerogel with hexadecanamide, FIG. 26C: a toluene xerogel with n-octadecanamide, FIG. 26D: a toluene xerogel with stearic acid amide/hexadecanamide/n-octanamide at a mixing ratio of 1/1/2 in terms of mass, FIG. 26E: a toluene xerogel with stearic acid amide/hexadecanamide/n-octanamide at a mixing ratio of 1/1/4 in terms of mass, FIG. 26F: a toluene xerogel with stearic acid amide/hexadecanamide/n-octanamide at a mixing ratio of 1/1/10 in terms of mass).

Comparative Example 13: Observation of Fine Structure of Gels Formed with Alkylamide Derivatives In the same procedure as in Comparative Example 1 to Comparative Example 3, three toluene gels were each formed with a single alkylamide derivative at a corresponding minimum gelation concentration. The resulting gels were dried in vacuo at room temperature to give xerogels, and the states of the obtained xerogels were observed under a scanning electron microscope (SEM). The obtained results are shown in FIG. 26 [FIG. 26A: a toluene xerogel with stearic acid amide, FIG. 26B: a toluene xerogel with hexadecanamide, FIG. 26C: a toluene xerogel with n-octanamide] and FIG. 27 [FIG. 27A: a toluene xerogel with stearic acid amide, FIG. 27B: a toluene xerogel with hexadecanamide, FIG. 27C: a toluene xerogel with n-octanamide]. The observation results of the states of the toluene gels before vacuum drying under a polarization microscope are shown in FIG. 27 [FIG. 27D: a toluene gel with 3 wt % stearic acid amide, FIG. 27E: a toluene gel with 3 wt % hexadecanamide, FIG. 27F: a toluene gel with 3 wt % n-octanamide].

Figure 27:
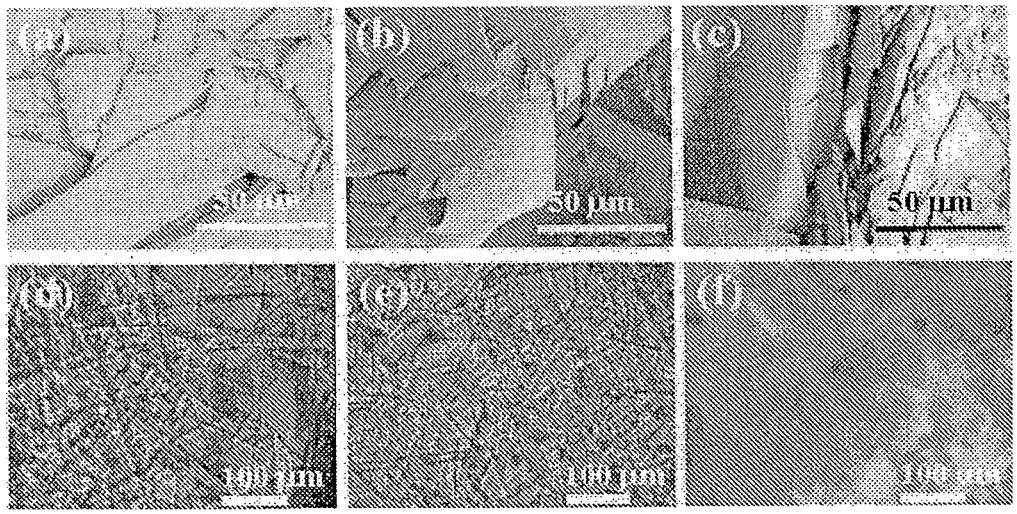
FIG. 27 includes scanning electron micrographs (SEM) of toluene xerogels with a single component of various alkylamide derivatives (prepared from gels at minimum gelation concentrations) and polarization micrographs of toluene gels in Comparative Example 13 (FIG. 27A: a toluene xerogel with stearic acid amide, FIG. 27B: a toluene xerogel with hexadecanamide, FIG. 27C: a toluene xerogel with n-octadecanamide, FIG. 27D: a toluene gel with 3 wt % stearic acid amide, FIG. 27E: a toluene gel with 6 wt % hexadecanamide, FIG. 27F: a toluene gel with 3 wt % n-octadecanamide).

As shown in FIGS. 26 and 27, it was ascertained that each toluene xerogel with a single alkylamide derivative is formed of a multi-layered sheet having a thickness of several hundreds of nanometers and a width of several tens of micrometers. It was also ascertained that each toluene gel with a single alkylamide derivative is formed of a network of sheet-like crystals corresponding to the result of the SEM observation.

Figure 28:
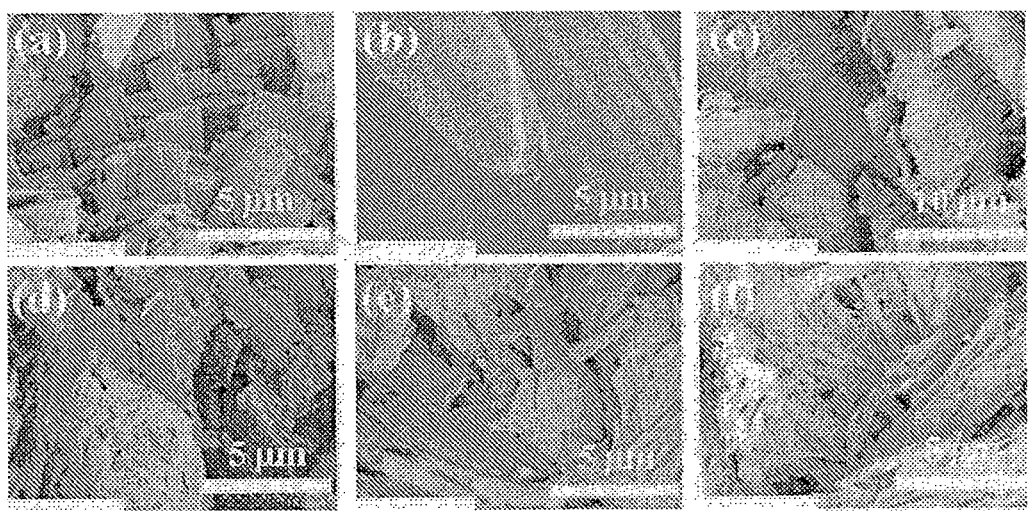
FIG. 28 includes scanning electron micrographs (SEM) of toluene xerogels with a single component of or with a mixture of various alkylurea derivatives (prepared from gels at minimum gelation concentrations) in Comparative Example 14 and Example 20 (FIG. 28A: a toluene xerogel with octadecylurea, FIG. 28B: a toluene xerogel with butylurea, FIG. 28C: a toluene xerogel with octadecylurea/butylurea at a mixing ratio of 1/1 in terms of mass, FIG. 28D: a toluene xerogel with octadecylurea/butylurea at a mixing ratio of 1/2 in terms of mass, FIG. 28E: a toluene xerogel with octadecylurea/butylurea at a mixing ratio of 1/4 in terms of mass, FIG. 28F: a toluene xerogel with octadecylurea/butylurea at a mixing ratio of 1/10 in terms of mass).

Comparative Example 14: Observation of Fine Structure of Gels Formed with Alkylurea Derivatives In the same procedure as in Comparative Example 4 and Comparative Example 5, two toluene gels were each formed with a single alkylurea derivative at a corresponding minimum gelation concentration. The resulting gels were dried in vacuo at room temperature to give xerogels, and the states of the obtained xerogels were observed under SEM. The obtained results are shown in FIG. 28 [FIG. 28A: a toluene xerogel with octadecylurea, FIG. 28B: a toluene xerogel with butylurea]. The observation results of the states of the toluene gels before vacuum drying under a polarization microscope are shown in FIG. 29 [FIG. 29A: a toluene gel with 2 wt % octadecylurea, FIG. 29B: a toluene gel with 6 wt % butylurea].

Figure 29:
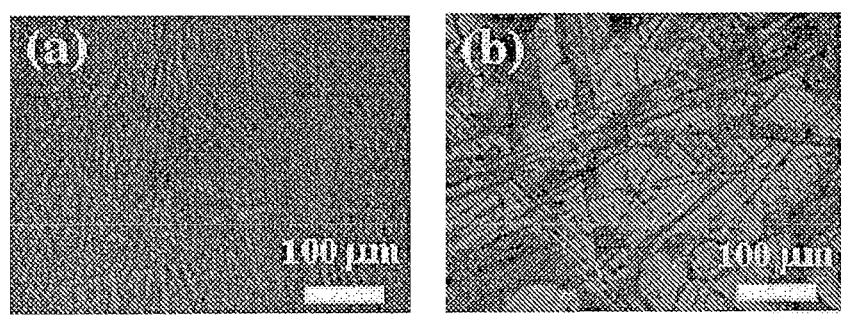
FIG. 29 includes polarization micrographs of toluene gels with a single component of various alkylurea derivatives in Comparative Example 14 (FIG. 29A: a toluene gel with 2 wt % octadecylurea, FIG. 29B: a toluene gel with 6 wt % butylurea).

As shown in FIGS. 28 and 29, it was ascertained that each toluene xerogel with the single alkylurea derivative is formed of a multi-layered sheet having a thickness of several hundreds of nanometers and a width of several tens of micrometers. It was also ascertained that each toluene gel with the single alkylurea derivative is formed of a network of sheet-like crystals corresponding to the result of the SEM observation.

It is known that a plate crystal of a clay mineral having a thickness of several nanometers and a width of several tens of micrometers and a plate-like wax crystal of an oil wax having a thickness of several hundreds of nanometers and a width of several tens of micrometers form a card-house structure including the sheet-like substances (plate-like crystals) as a skeleton, and the card-house structure holds water or organic solvents in its voids, giving a solvent-containing solid (reference literature: (1) "Clay handbook", Gihodo Shuppan Co., Ltd., (2009), (2) "Gel control—gel preparation and control of gelation—", Johokiko Co., Ltd., (2009), pp. 15-17, (3) Colloids and Surfaces, vol. 51, (1990), pp. 219-238, for example).

In other words, the above results that the dried gel (xerogel) of the gel formed from toluene as the medium with the alkylamide derivative or the alkylurea derivative as the gelator had a multi-layered sheet structure is thought to be as follows: the toluene gel formed with the alkylamide derivative or the alkylurea derivative as the gelator has a card-house structure, and the card-house structure holds solvents in its voids, resulting in gel formation. The multi-layered sheet structure is assumed to be formed by aggregation of the sheet-like substances that form the card-house structure in a drying process.

Example 19: Observation of Fine Structure of Gels Formed with Mixture of Alkylamide Derivatives In the same procedure as in Example 3, toluene gels with a mixture of three alkylamide derivatives were prepared. The resulting gels were dried in vacuo at room temperature to give xerogels, and the states of the obtained xerogels were observed under SEM. The obtained results are shown in FIG. 26 [FIG. 26D: a toluene xerogel with stearic acid amide/hexadecanamide/n-octanamide at a mixing ratio of 1/1/2 in terms of mass, FIG. 26E: a toluene xerogel with stearic acid amide/hexadecanamide/n-octanamide at a mixing ratio of 1/1/4 in terms of mass, FIG. 26F: a toluene xerogel with stearic acid amide/hexadecanamide/n-octanamide at a mixing ratio of 1/1/10 in terms of mass]. As shown in FIG. 26, it was ascertained that as the mixture contains n-octanamide having a short alkyl chain at a higher ratio, sheet-like crystals having a length of several tens of micrometers and a thickness of submicrometer are changed to flaky crystals having a length of several micrometers and a thickness of submicrometer, resulting in a higher density of the network forming the gel.

Example 20: Observation of Fine Structure of Gels Formed with Mixture of Alkylurea Derivatives In the same procedure as in Example 11, toluene gels with a mixture of two alkylurea derivatives were prepared. The resulting gels were dried in vacuo at room temperature to give xerogels, and the states of the obtained xerogels were observed under SEM. The obtained results are shown in FIG. 28 [FIG. 28C: a toluene xerogel with octadecylurea/butylurea at a mixing ratio of 1/1 in terms of mass, FIG. 28D: a toluene xerogel with octadecylurea/butylurea at a mixing ratio of 1/2 in terms of mass, FIG. 28E: a toluene xerogel with octadecylurea/butylurea at a mixing ratio of 1/4 in terms of mass, FIG. 28F: a toluene xerogel with octadecylurea/butylurea at a mixing ratio of 1/10 in terms of mass].

As shown in FIG. 28, it was ascertained that as the mixture contains butylurea having a short alkyl chain at a higher ratio, sheet-like crystals having a length of several micrometers and a thickness of submicrometer are changed to tape-like or fibrous crystals having a length of several micrometers and a thickness of submicrometer, resulting in a higher density of the network forming the gel.

Figure 30:
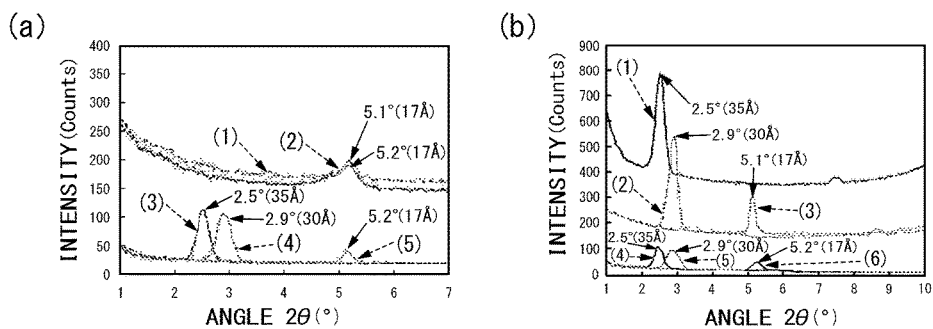
FIG. 30 includes views showing the results of X-ray diffraction analysis in a small angle region of toluene gels with a single alkylamide derivative, toluene gels with a mixture of three alkylamide derivatives, and crystals of alkylamide derivatives in Example 21 (FIG. 30A: (1) a toluene gel with 4 wt % stearic acid amide/hexadecanamide/n-octanamide at a mixing ratio of 1/1/4 in terms of mass, (2) a toluene gel with 4 wt % stearic acid amide/hexadecanamide/n-octanamide at a mixing ratio of 1/1/10 in terms of mass, (3) a crystal sample of stearic acid amide, (4) a crystal sample of hexadecanamide, (5) a crystal sample of n-octanamide.

Example 21: X-Ray Diffraction Analysis of Gels with Mixture of Alkylamide Derivatives The above-mentioned toluene gels with a mixture of three alkylamide derivatives were subjected to X-ray diffraction analysis in a small angle region. In a similar manner, crystal samples (reagent grade) of three alkylamide derivatives before gelation and the gels with a single alkylamide derivative were subjected to X-ray diffraction analysis. The obtained results are shown in FIG. 30 [FIG. 30A: (1) a toluene gel with 4 wt % stearic acid amide/hexadecanamide/n-octanamide at a mixing ratio of 1/1/4 in terms of mass, (2) a toluene gel with 4 wt % stearic acid amide/hexadecanamide/n-octanamide at a mixing ratio of 1/1/10 in terms of mass, (3) a crystal sample of stearic acid amide, (4) a crystal sample of hexadecanamide, (5) a crystal sample of n-octanamide; FIG. 30B: (1) a crystal sample of stearic acid amide, (2) a crystal sample of hexadecanamide, (3) a crystal sample of n-octanamide, (4) a toluene gel with 3 wt % stearic acid amide, (5) a toluene gel with 6 wt % hexadecanamide, (6) a toluene gel with 3 wt % n-octanamide].

Figure 31:
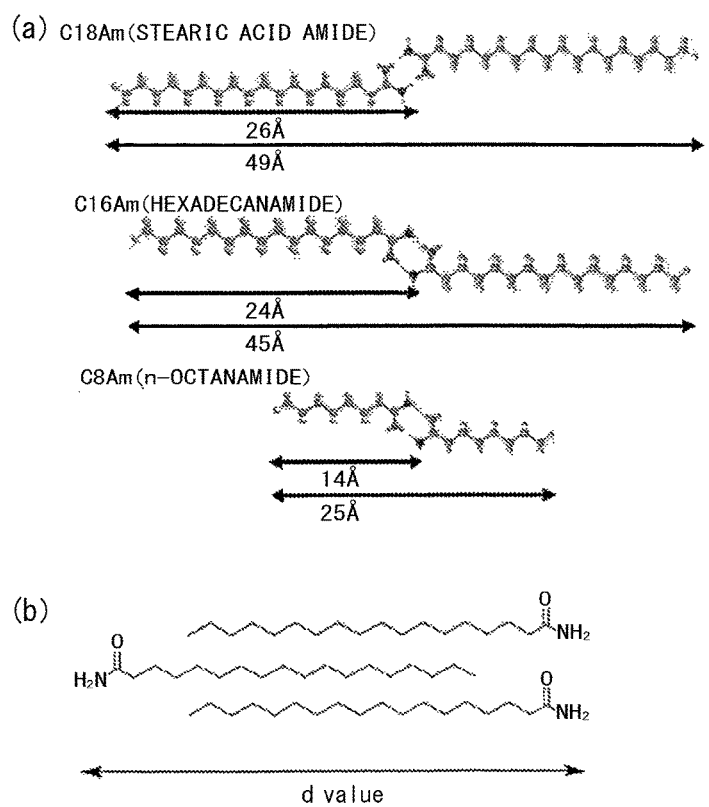
FIG. 31A is a view showing molecular models (the molecular length is calculated by ChemDraw3D and includes van der Waals radii of two amino groups and two methyl groups; the van der Waals radii are according to literatures (J. Phys. Chem., (1964), vol. 68, p. 441-451 and J. Phys. Chem., (1996), vol. 100, p. 7384-7391) of alkylamide derivatives (stearic acid amide, hexadecanamide, n-octanamide) and dimers configured so as to form hydrogen bonds.
FIG. 31B is a view showing a lamella structure which the alkylamide derivatives can form.

FIG. 31 shows molecular models (the molecular length is calculated by ChemDraw3D) of three alkylamide derivatives.

As shown in FIG. 30B, it was ascertained that the peaks of the crystal samples ((1) to (3)) of the alkylamide derivatives are in good agreement with those of the corresponding toluene gels ((4) to (6)) with a single derivative. As shown in FIG. 30A, as the mixture contained n-octanamide having a short alkyl chain at a higher ratio, the peak assigned to n-octanamide became observable. These results revealed that the network of the toluene gel with a mixture of three components is mainly formed of flaky crystals of n-octanamide.

According to the literature (Acta Cryst., (1955), vol. 8, pp. 551-557), it was observed that an alkylamide derivative (tetradecanamide) in a crystal state formed a dimer through hydrogen bonds (for example, see FIG. 31). However, the molecular lengths of the dimers of the alkylamide derivatives as shown in FIG. 31A do not match the experimental results in the present example. The peaks determined by the X-ray diffraction analysis are assumed to be obtained by the diffraction analysis of a lamella structure as shown in FIG. 31B.

Example 22: X-Ray Diffraction Analysis of Gels with Mixture of Alkylurea Derivatives The above-mentioned toluene gels with a mixture of two alkylurea derivatives were subjected to X-ray diffraction analysis in a small angle region. In a similar manner, crystal samples of two alkylurea derivatives before gelation and the gels with a single alkylurea derivative were subjected to X-ray diffraction analysis. The obtained results are shown in FIG. 32 [FIG. 32A: (1) a toluene gel with 3 wt % octadecylurea/butylurea at a mixing ratio of 1/1 in terms of mass, (2) a toluene gel with 3 wt % octadecylurea/butylurea at a mixing ratio of 1/2 in terms of mass, (3) a crystal sample of octadecylurea, (4) a crystal sample of butylurea; FIG. 32B: (1) a toluene gel with 3 wt % octadecylurea/butylurea at a mixing ratio of 1/4 in terms of mass, (2) a toluene gel with 3 wt % octadecylurea/butylurea at a mixing ratio of 1/10 in terms of mass, (3) a crystal sample of octadecylurea, (4) a crystal sample of butylurea; FIG. 32C: (1) a crystal sample of octadecylurea, (2) a crystal sample of butylurea; FIG. 32D: (1) a toluene gel with 2 wt % octadecylurea, (2) a toluene gel with 6 wt % butylurea].

FIG. 33A shows molecular models (the molecular length is calculated by ChemDraw3D) of two alkylurea derivatives, and FIG. 33B shows a lamella structure of octadecylurea suggested by a literature (Chemistry A European Journal, (2005), vol. 11, pp. (3243-3254).

As shown in FIGS. 32C and 32D, the peaks of the crystal samples of octadecylurea and butylurea do not match those of the gels with a single component, and it is assumed that the urea in the gel state has the lamella structure shown in FIG. 33 (b) and shows a diffraction peak in a shorter cycle region.

As shown in FIGS. 32A and 32B, as the toluene gel with a mixture of two components contains butylurea having a short alkyl chain at a higher ratio, the peak assignable to butylurea becomes observable, whereas the peak assignable to octadecylurea decreases. These results revealed that the network of the toluene gel with a mixture of two components is mainly formed of tape-like crystals or fibrous crystals of butylurea.

The results from Example 19 to Example 22 revealed that as the gel with a mixture of alkylamide derivatives or a mixture of alkylurea derivatives contains an alkylamide derivative (n-octylamide) or an alkylurea derivative (butylurea) having a short alkyl chain at a higher ratio, sheet-like crystals forming the network of the gel are changed to smaller flaky crystals or fibrous crystals, and thus the network has smaller meshes, resulting in a higher density of the network.

An improvement in network density of such a gel with a mixture of alkylamide derivatives or a mixture of alkylurea derivatives is thought to contribute to an improvement in mechanical properties (thixotropic properties) and other properties of the gel with the mixture, in a similar manner to that an improvement in network density of a polymer network contributes to an improvement in mechanical strength and other properties. An improvement in transparency is also assumed to be as follows: the network includes components having a width of submicrometer, which is shorter than the wavelength of light, and thus light is prevented from scattering.

The invention claimed is:

1. A gelator characterized by comprising:
two or more alkylamide compounds of General Formula [I]:

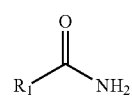

(where $R_1$ is a $C_{1-30}$ aliphatic group optionally having a substituent), comprising an alkylamide compound of Formula [I] where $R_1$ is a $C_{5-7}$ aliphatic group optionally having a substituent and an alkylamide compound of Formula [I] where $R_1$ is a $C_{11-21}$ aliphatic group optionally having a substituent, or two or more alkylurea compounds of General Formula [II]:

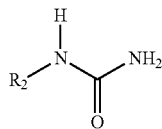

(where $R_2$ is a $C_{1-30}$ aliphatic group optionally having a substituent), comprising an alkylurea compound of Formula [II] where $R_2$ is a $C_{4-8}$ aliphatic group optionally having a substituent and an alkylurea compound of Formula [II] where $R_2$ is a $C_{12-18}$ aliphatic group optionally having a substituent, characterized in that a gel comprising the gelator exhibits thixotropic properties.

2. The gelator according to claim 1, comprising two alkylamide compounds of Formula [I], wherein an alkylamide compound (A) having $R_1$ with a larger number of carbon atoms and an alkylamide compound (B) having $R_1$ with a smaller number of carbon atoms are contained in a mass ratio of (A):(B)=1 to 20:20 to 1.

3. The gelator according to claim 1, comprising three alkylamide compounds of Formula [I], wherein an alkylamide compound (C) having $R_1$ with the largest number of carbon atoms, an alkylamide compound (D) having $R_1$ with a smaller number of carbon atoms than the number of carbon atoms of the alkylamide compound (C), and an alkylamide compound (E) having $R_1$ with a smaller number of carbon atoms than the number of carbon atoms of the alkylamide compound (D) are contained in a mass ratio of (C):(D):(E) =1 to 5:1 to 5:1 to 20.

4. The gelator according to claim 1, comprising two alkylurea compounds of Formula [II], wherein an alkylurea compound (A) having $R_2$ with a larger number of carbon atoms and an alkylurea compound (B) having $R_2$ with a smaller number of carbon atoms are contained in a mass ratio of (A):(B)=1 to 20:20 to 1.

5. A gel characterized by comprising:

two or more alkylamide compounds of General Formula [I]:

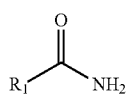

(where $R_1$ is a $C_{1-30}$ aliphatic group optionally having a substituent), comprising an alkylamide compound of formula [I] where $R_1$ is a $C_{5-7}$ aliphatic group optionally having a substituent and an alkylamide compound of Formula [I] where $R_1$ is a $C_{11-21}$ aliphatic group optionally having a substituent, or two or more alkylurea compounds of General Formula [II]:

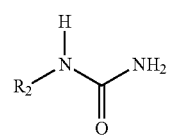

(where $R_2$ is a $C_{1-30}$ aliphatic group optionally having a substituent), comprising an alkylurea compound of Formula [II] where $R_2$ is a $C_{4-8}$ aliphatic group optionally having a substituent and an alkylurea compound of [II] where $R_2$ is a $C_{12-18}$ aliphatic group optionally having a substituent, characterized in that the gel exhibits thixotropic properties.

6. The gelator according to claim 1, comprising two alkylamide compounds of Formula [I], wherein an alkylamide compound (A) having $R_1$ with a larger number of carbon atoms and an alkylamide compound (B) having $R_1$ with a smaller number of carbon atoms are contained in a mass ratio of (A):(B)=1 to 20:20 to 1.

7. The gelator according to claim 1, comprising three alkylamide compounds of Formula [I], wherein an alkylamide compound (C) having $R_1$ with the largest number of carbon atoms, an alkylamide compound (D) having $R_1$ with a smaller number of carbon atoms than the number of carbon atoms of the alkylamide compound (C), and an alkylamide compound (E) having $R_1$ with a smaller number of carbon atoms than the number of carbon atoms of the alkylamide compound (D) are contained in a mass ratio of (C):(D):(E) =1 to 5:1 to 5:1 to 20.

8. The gelator according to claim 1, comprising two alkylurea compounds of Formula [II], wherein an alkylurea compound (A) having $R_2$ with a larger number of carbon atoms and an alkylurea compound (B) having $R_2$ with a smaller number of carbon atoms are contained in a mass ratio of (A):(B)=1 to 20:20 to 1.

9. The gelator according to claim 1, wherein the two or more alkylamide compounds or the two or more alkylurea compounds are homologous alkyl compounds having different chain lengths.

10. The gel according to claim 5, wherein the two or more alkylamide compounds or the two or more alkylurea compounds are homologous alkyl compounds having different chain lengths.

* * * * *